United States Patent
Jung et al.

(10) Patent No.: US 11,730,377 B2
(45) Date of Patent: Aug. 22, 2023

(54) ELECTRONIC DEVICE AND METHOD FOR PROVIDING INFORMATION ON CARDIOVASCULAR STATE OF USER

(71) Applicant: Samsung Electronics Co., Ltd., Suwon-si (KR)

(72) Inventors: Sunok Jung, Suwon-si (KR); Yongjin Lee, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 290 days.

(21) Appl. No.: 16/975,101

(22) PCT Filed: Jan. 14, 2019

(86) PCT No.: PCT/KR2019/000535
§ 371 (c)(1),
(2) Date: Aug. 21, 2020

(87) PCT Pub. No.: WO2019/164126
PCT Pub. Date: Aug. 29, 2019

(65) Prior Publication Data
US 2020/0397311 A1 Dec. 24, 2020

(30) Foreign Application Priority Data
Feb. 21, 2018 (KR) .................. 10-2018-0020733

(51) Int. Cl.
*A61B 5/0205* (2006.01)
*A61B 5/024* (2006.01)
*A61B 5/00* (2006.01)

(52) U.S. Cl.
CPC ............ *A61B 5/0205* (2013.01); *A61B 5/024* (2013.01); *A61B 5/681* (2013.01); *A61B 5/6824* (2013.01); *A61B 5/743* (2013.01); *A61B 5/7455* (2013.01)

(58) Field of Classification Search
CPC ....... A61B 5/0205; A61B 5/024; A61B 5/681; A61B 5/6824; A61B 5/743; A61B 5/7455;
(Continued)

(56) References Cited

U.S. PATENT DOCUMENTS

2011/0251513 A1  10/2011  Chetham et al.
2014/0031643 A1  1/2014  An et al.
(Continued)

FOREIGN PATENT DOCUMENTS

JP  2009-066269 A  4/2009
JP  2010-526604 A  8/2010
(Continued)

OTHER PUBLICATIONS

American Heart Association, last reviewed Jul. 31, 2015, accessed on Aug. 26, 2022, accessed at https://www.heart.org/en/health-topics/high-blood-pressure/the-facts-about-high-blood-pressure/all-about-heart-rate-pulse (Year: 2015).*

(Continued)

*Primary Examiner* — Eric F Winakur
*Assistant Examiner* — Jonathan Drew Moroneso

(57) ABSTRACT

An electronic device according to various embodiments may comprise: a memory storing instructions; at least one biometric sensor; a display; and at least one processor, wherein the at least one processor is configured to execute the stored instructions in order to: obtain biometric information of a user related with the electronic device by using the at least one biometric sensor; obtain first data indicating a cardiovascular state of the user from the biometric information; obtain second data indicating a relative difference between the first data and reference data indicating a cardiovascular state in a resting state of the user; and display, by using the (Continued)

display, an indication for indicating a health status of the user, on the basis at least of the second data.

18 Claims, 19 Drawing Sheets

(58) Field of Classification Search
CPC .............. A61B 5/6898; A61B 5/02007; A61B 5/02416; A61B 5/7235
See application file for complete search history.

(56) References Cited

U.S. PATENT DOCUMENTS

| | | | |
|---|---|---|---|
| 2015/0126822 A1* | 5/2015 | Chavan | A61B 5/0205 600/595 |
| 2015/0288797 A1* | 10/2015 | Vincent | G16H 10/60 455/404.2 |
| 2016/0094700 A1* | 3/2016 | Lee | H04W 4/80 455/419 |
| 2016/0196635 A1* | 7/2016 | Cho | G06T 3/40 345/660 |
| 2016/0249864 A1* | 9/2016 | Kang | A61B 5/02055 340/870.07 |
| 2016/0259905 A1* | 9/2016 | Park | G16Z 99/00 |
| 2017/0112395 A1 | 4/2017 | Kim et al. | |
| 2017/0293727 A1 | 10/2017 | Klaassen et al. | |
| 2018/0014755 A1* | 1/2018 | Alessandri | G16H 40/63 |

FOREIGN PATENT DOCUMENTS

| | | |
|---|---|---|
| JP | 2015-529488 A | 10/2015 |
| KR | 10-2013-0010207 A | 1/2013 |
| KR | 10-2016-0108051 A | 9/2016 |
| KR | 10-2017-0018536 A | 2/2017 |
| KR | 10-2017-0048970 A | 5/2017 |
| KR | 10-1809131 B1 | 12/2017 |

OTHER PUBLICATIONS

Korean Intellectual Property Office, "Notice of Preliminary Rejection," issued Jun. 20, 2022, in connection with Korean Patent Application No. KR10-2018-0020733, 16 pages.

Whelton et al., "2017 ACC/AHA/AAPA/ABC/ACPM/AGS/APhA/ASH/ASPC/NMA/PCNA Guideline for the Prevention, Detection, Evaluation, and Management of High Blood Pressure in Adults", 2017 High Blood Pressure Clinical Guideline, Oct. 23, 2018, 111 pages.

International Search Report dated Apr. 18, 2019 in connection with International Patent Application No. PCT/KR2019/000535, 2 pages.

Written Opinion of the International Searching Authority dated Apr. 18, 2019 in connection with International Patent Application No. PCT/KR2019/000535, 5 pages.

Notice of Patent Grant dated Nov. 14, 2022 in connection with Korean Patent Application No. 10-2018-0020733, 3 pages.

* cited by examiner

ELECTRONIC DEVICE AND METHOD FOR PROVIDING INFORMATION ON CARDIOVASCULAR STATE OF USER

CROSS-REFERENCE TO RELATED APPLICATIONS

This application is a 371 of International Application No. PCT/KR2019/000535 filed on Jan. 14, 2019, which claims priority to Korean Patent Application No. 10-2018-0020733 filed on Feb. 21, 2018, the disclosures of which are herein incorporated by reference in their entirety.

BACKGROUND

1. Field

Various embodiments described below relate to an electronic device for presenting information on a cardiovascular state of a user and a method thereof.

2. Description of Related Art

Owing to an increase of a concern about health, an electronic device including a biometric sensor is being developed. This electronic device can acquire biometric information on human, and present information related with the health of human by using the acquired biometric information.

A cardiovascular disease such as hypertension, ischemic heart disease, coronary artery disease, angina, myocardial infarction, atherosclerosis, arrhythmia, cerebrovascular disease, stroke, arrhythmia, etc. would be lain latent and suddenly caused, thus taking away a human's life.

On the other hand, modern people can carry one or more electronic devices in daily life. Accordingly, there can be a demand for an electronic device getting information on a cardiovascular state and presenting information related with the information on the cardiovascular state.

Technological solutions the present document seeks to achieve are not limited to the above-mentioned technological solutions, and other technological solutions not mentioned above would be able to be clearly understood by a person having ordinary skill in the art from the following statement.

SUMMARY

An electronic device of various embodiments may include a housing, a display exposed through a first portion of the housing, a photoplethysmogram (PPG) sensor exposed through a second portion of the housing, a processor located in the housing and operatively connected with the display and the PPG sensor, a memory located in the housing and operatively connected with the processor. The memory may store instructions of, at execution, allowing the processor to, in a first operation, receive first data by using the PPG sensor and determine a plurality of reference ranges of a blood pressure on the basis at least in part of the first data, and store the plurality of reference ranges, and in a second operation, after the first operation, receive second data by using the PPG sensor, and select one reference range among the plurality of reference ranges on the basis at least in part of the second data, and present at least one of a graphical user interface (GUI), a text, or a numerical value in order to indicate the selected reference range among the plurality of reference ranges on the display.

An electronic device of various embodiments may include a memory storing instructions, at least one biometric sensor, a display, and at least one processor. The at least one processor may be configured to execute the stored instructions in order to obtain biometric information of a user related with the electronic device by using the at least one biometric sensor, obtain first data indicating a cardiovascular state of the user from the biometric information, obtain second data indicating a relative difference between the first data and reference data indicating a cardiovascular state in a resting state of the user, and display, by using the display, an indication for indicating a health status of the user, on the basis at least of the second data.

An electronic device of various embodiments may include a memory storing instructions, a communication module, a display, and at least one processor. The at least one processor may be configured to execute the stored instructions in order to receive first data indicating a cardiovascular state of a user which has been obtained on the basis of biometric information of the user obtained through at least one biometric sensor of another electronic device, from the another electronic device interworking with the electronic device and worn by the user related with the electronic device, obtain second data indicating a relative difference between the first data and reference data indicating a cardiovascular state in a resting state of the user, obtain an input for executing an application presenting a service related with a health stored in the electronic device, and display, through the display, an indication for indicating the health status of the user, by using the second data, on the basis of the obtaining.

An electronic device of various embodiments may include a memory storing instructions, at least one biometric sensor, a display, and at least one processor. The at least one processor may be configured to execute the stored instructions in order to obtain data indicating a cardiovascular state of a user related with the electronic device by using the at least one biometric sensor, identify that a relative difference between the data and reference data indicating a cardiovascular state in a resting state of the user is changed, and change at least part of an indication indicating the relative difference indicated using the display, on the basis of the identification.

A method of an electronic device of various embodiments may include a first operation of receiving first data by using the PPG sensor and determining a plurality of reference ranges of a blood pressure on the basis at least in part of the first data, and storing the plurality of reference ranges, and a second operation of, after the first operation, receiving second data by using the PPG sensor, and selecting one reference range among the plurality of reference ranges on the basis at least in part of the second data, and presenting at least one of a graphical user interface (GUI), a text, or a numerical value in order to indicate the selected reference range among the plurality of reference ranges on the display.

A method of an electronic device of various embodiments may include obtaining biometric information of a user related with the electronic device by using the at least one biometric sensor of the electronic device, obtaining first data indicating a cardiovascular state of the user from the biometric information, obtaining second data indicating a relative difference between the first data and reference data indicating a cardiovascular state in a resting state of the user, and displaying, by using the display of the electronic device, an indication for indicating a health status of the user, on the basis at least of the second data.

A method of an electronic device of various embodiments may include receiving first data indicating a cardiovascular state of a user which is obtained on the basis of biometric information of the user obtained through at least one biometric sensor of another electronic device, from the another electronic device interworking with the electronic device and worn by the user related with the electronic device, obtaining second data indicating a relative difference between the first data and reference data indicating a cardiovascular state in a resting state of the user, obtaining an input for executing an application presenting a service related with a health stored in the electronic device, and displaying, through the display of the electronic device, an indication for indicating the health status of the user, by using the second data, on the basis of the obtaining.

A method of an electronic device of various embodiments may include obtaining data indicating a cardiovascular state of a user related with the electronic device by using the at least one biometric sensor of the electronic device, identifying that a relative difference between the data and reference data indicating a cardiovascular state in a resting state of the user is changed, and changing at least part of an indication indicating the relative difference indicated using the display of the electronic device, on the basis of the identification.

By obtaining a cardiovascular state of a user, an electronic device of various embodiments and a method thereof may present information on a health status of the user.

An effect obtainable from the disclosure is not limited to the above-mentioned effects, and other effects not mentioned will be able to be apparently understood from the following statement by a person having ordinary skill in the art to which the disclosure pertains.

DETAILED DESCRIPTION

Figure 1:
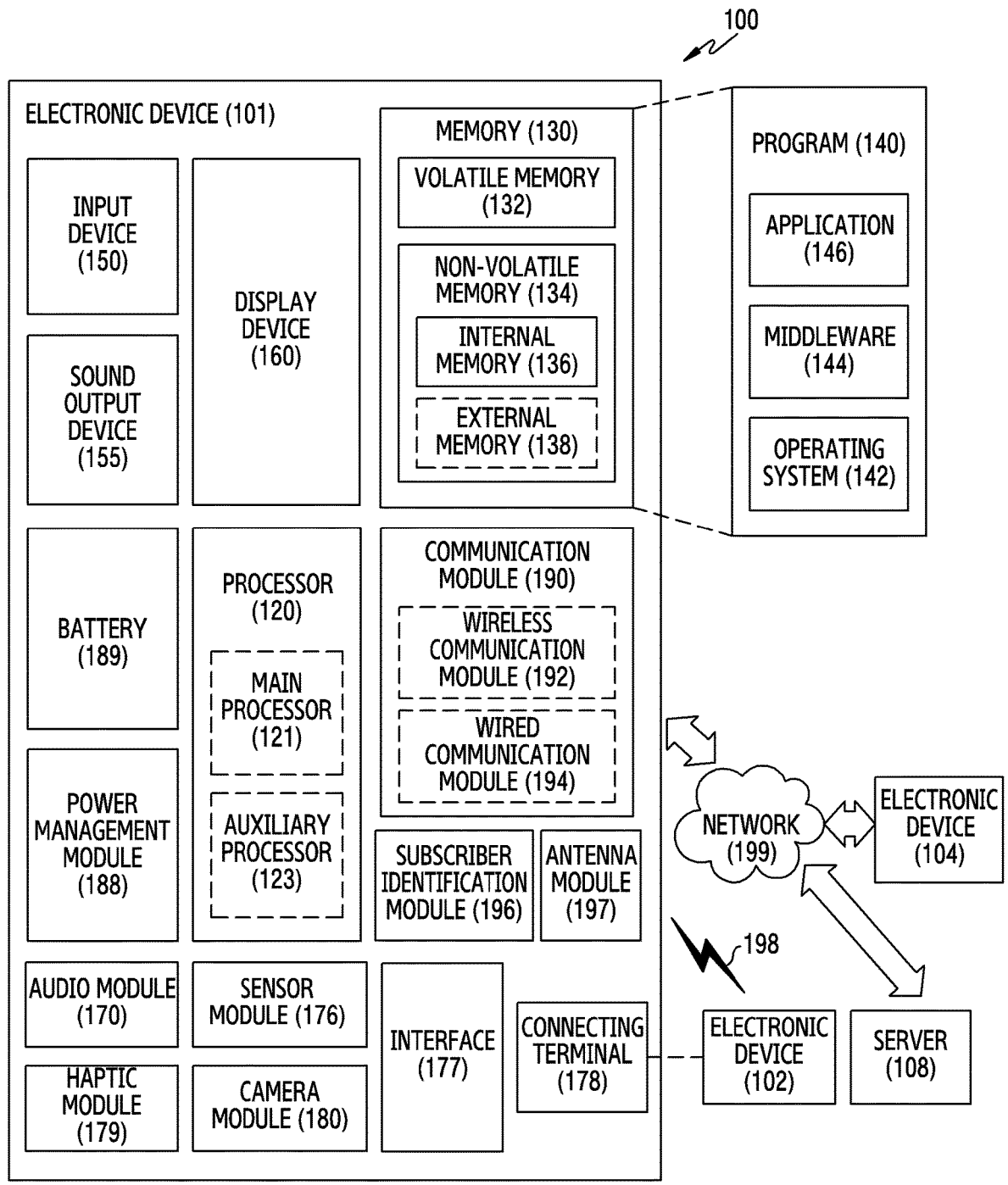
FIG. 1 is a block diagram of an electronic device 101 within a network environment 100 according to various embodiments.

FIG. 1 is a block diagram illustrating an electronic device 101 in a network environment 100 according to various embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor

120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123. The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as BLUETOOTH™, wireless-fidelity (Wi-Fi) direct, or infrared data association (IrDA)) or the second network 199

(e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other.

According to an embodiment, the wireless communication module 192 may identify and authenticate the electronic device 101 in a communication network using user information stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PLAYSTORE™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

Figure 2:
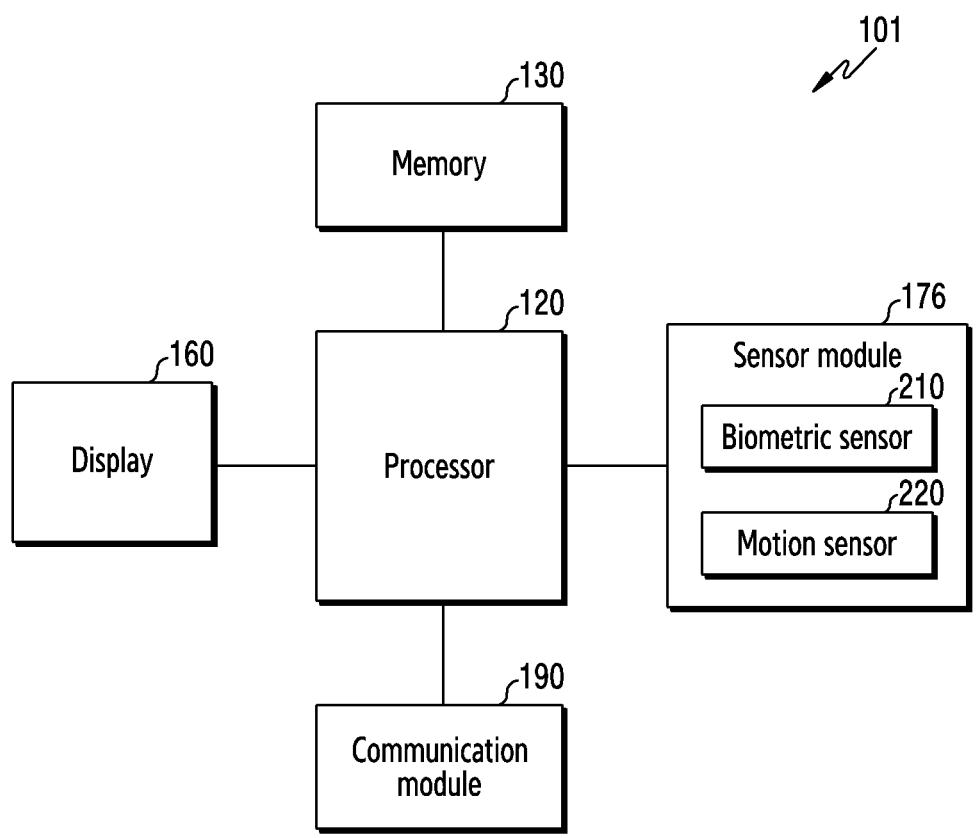
FIG. 2 illustrates an example of a functional construction of an electronic device according to various embodiments.

FIG. 2 illustrates an example of a functional construction of an electronic device according to various embodiments. This functional construction may be included in the electronic device 101 illustrated in FIG. 1.

Referring to FIG. 2, the electronic device 101 may include a processor 120, a memory 130, a display 160, a sensor module 176, and a communication module 190.

In various embodiments, the processor 120 may include the processor 120 shown in FIG. 1, and the memory 130 may include the memory 130 shown in FIG. 1, and the display 160 may include the display device 160 shown in FIG. 1, and the sensor module 176 may include the sensor module 176 shown in FIG. 1, and the communication module 190 may include the communication module 190 shown in FIG. 1.

In various embodiments, the processor 120, the memory 130, the display 160, the sensor module 176, and the communication module 190 may be installed in a housing of the electronic device 101. In various embodiments, the housing may be implemented in the form of portability or be implemented in the form of being included in a specific device.

The processor 120 may control a general operation of the electronic device 101. The processor 120 may execute applications presenting an advertisement service, an Internet service, a game service, a video service, a health care service, etc.

The whole of the processor 120 or a part thereof may be electrically or operatively coupled with or connected to another component (e.g., the memory 130, the display 160, the sensor module 176, or the communication module 190) within the electronic device 101.

The display 160 may output contents, data, or a signal. In various embodiments, the display 160 may display image data which has been processed by the processor 120. For example, the display 160 may display a capture or still image. For another example, the display 160 may display a video or camera preview image. For further example, the display 160 may display a graphical user interface (GUI) wherein a user may interact with the electronic device 101.

The sensor module 176 may be used to identify a state of the electronic device 101 or a state of a user related with the electronic device 101.

The sensor module 176 may include at least one biometric sensor 210 and at least one motion sensor 220.

The at least one biometric sensor 210 may be used to obtain or get data on a cardiovascular state of a user related with the electronic device 101. For example, the at least one biometric sensor 210 may be used to obtain a blood pressure of the user related with the electronic device 101, a blood sugar, a heart rate, a stress level (e.g., a heart rate variability), or an oxygen saturation ($SpO_2$). In various embodiments, the at least one biometric sensor 210 may include at least one or more of an electrocardiogram (ECG) sensor, a photoplethysmography (PPG) sensor, or a ballistocardiogram (BCG) sensor.

To get in contact with at least part of the body of a user related with the electronic device 101, the at least one biometric sensor 210 may be exposed out.

In response to the at least one biometric sensor 210 including the PPG sensor, the at least one biometric sensor 210 may include an emitter and a receiver. To obtain data indicating a cardiovascular state of a user, the emitter may emit light. The light may include one or more of infrared light or visible light. The light may be reflected by at least part of the body of the user related with the electronic device 101. The receiver may receive the reflected light. The receiver may change or convert the received light into an electrical signal. For the sake of the change or conversion, the receiver may include at least one photodiode. In various embodiments, the electrical signal may be configured with an analog signal.

The at least one biometric sensor 210 may convert the analog signal into a digital signal, by using an analog-to-digital converter (ADC) within the sensor. The at least one biometric sensor 210 may present information on the digital signal to the processor 120.

The at least one motion sensor 220 may be used to obtain a change of movement of the electronic device 101. For example, to identify a body condition of a user related with the electronic device 101, the at least one motion sensor 220 may be used to obtain the change of the movement of the electronic device 101. In various embodiments, the at least one motion sensor 220 may include a gesture sensor, an image sensor (e.g., a camera module), a gyro sensor, an acceleration sensor, a grip sensor, a proximity sensor, etc.

In various embodiments, the processor 120 may obtain reference data indicating a cardiovascular state in a resting state of a user related with the electronic device 101. The reference data may be used for comparison with data on a cardiovascular state of the user obtained during a user's daily life. In various embodiments, the resting state may mean a state in which the user does not move during a specified time (e.g., five minutes or more) or a state in which the user moves minutely during the specified time. In various embodiments, the resting state may mean that the user is in an aerobic exercise state. In various embodiments, the resting state may mean a state of right after sleep. In various embodiments, the resting state may mean a state in which the user is right before rising. In various embodiments, the processor 120 may obtain the reference data which has been measured while the user is in the resting state. The reference data may be identified on the basis of at least one of a systolic blood pressure in the resting state of the user, a mean arterial pressure in the resting state of the user, a diastolic blood pressure in the resting state of the user, a cardiac output in the resting state of the user, a total peripheral resistance in the resting state of the user, or a heart rate of the resting state of the user. However, an embodiment is not limited to this.

In various embodiments, the processor 120 may obtain the reference data from an external electronic device. For example, the processor 120 may receive the reference data which has been obtained using at least one biometric sensor of another electronic device 102, from the another electronic device 102 associated with the electronic device 101. For another example, the processor 120 may receive the reference data from a server (e.g., a server presenting a health care service or a server of a hospital) related with a user.

In various embodiments, the processor 120 may obtain the reference data by using the at least one biometric sensor 210. For example, the processor 120 may obtain biometric information of a user of a resting state, through the at least one biometric sensor 210, and obtain the reference data on the basis of the obtained biometric information. In various embodiments, the biometric information may include one or more of blood pressure information of the user, blood sugar information of the user, heart rate information of the user, a stress level of the user, or an oxygen saturation of the user. However, an embodiment is not limited to this. In various embodiments, to induce the resting state of the user, the processor 120 may display, by using the display 160, guidance information for guiding the resting state of the user, while obtaining the biometric information of the user by using the at least one biometric sensor 210 or right before obtaining the biometric information of the user by using the at least one biometric sensor 210.

In various embodiments, the processor 120 may obtain the reference data by using a camera. For example, by photographing an image or document including the reference data through the camera of the electronic device 101, the processor 120 may obtain the image including the reference data or, by recognizing the obtained image, the processor 120 may obtain the reference data.

In various embodiments, the processor 120 may obtain biometric information of a user related with the electronic device 101, by using the at least one biometric sensor 210. In various embodiments, the biometric information may include one or more of blood pressure information of the user, blood sugar information of the user, heart rate information of the user, a stress level of the user, or an oxygen saturation of the user. However, an embodiment is not limited to this. In various embodiments, the processor 120 may obtain first data indicating a cardiovascular state of the user from the biometric information. For example, by performing pulse wave analysis using the biometric information, the processor 120 may obtain the first data indicating the cardiovascular state of the user. In various embodiments, the first data may be identified on the basis of at least one of a systolic blood pressure obtained from the biometric information, a mean arterial pressure obtained from the biometric information, a diastolic blood pressure obtained from the biometric information, a cardiac output obtained from the biometric information, a total peripheral resistance obtained from the biometric information, or a heart rate obtained from the biometric information. However, an embodiment is not limited to this.

In various embodiments, the processor 120 may obtain second data which indicates a relative difference between the reference data and the first data. In various embodiments, the relative difference may include a ratio of the reference data and the first data, a difference between the reference data and the first data, or a variation between the reference data and the first data. However, an embodiment is not limited to this. In various embodiments, the second data may be indicated through various methods. For example, the second data may mean a ratio of the reference data related with the systolic blood pressure and the first data related with the diastolic blood pressure. For another example, the second data may mean a ratio of the reference data related with the mean arterial pressure and the first data related with the mean arterial pressure. For further example, the second data may mean a ratio of the reference data (e.g., a value obtained by a multiplication of the systolic blood pressure and the heart rate) identified on the basis of the systolic blood pressure and the heart rate and the first data identified on the basis of the systolic blood pressure and the heart rate. For yet another example, the second data may mean a ratio of the reference data related with the diastolic blood pressure and the first data related with the diastolic blood pressure. For still another example, the second data may mean a ratio of the reference data (e.g., a value obtained by a multiplication of the diastolic blood pressure and the heart rate) identified on the basis of the diastolic blood pressure and the heart rate and the first data identified on the basis of the diastolic blood pressure and the heart rate. For still another example, the second data may mean a ratio of the reference data related with the cardiac output and the first data related with the cardiac output. For still another example, the second data may mean a ratio of the reference data related with the total peripheral resistance and the first data related with the total peripheral resistance. For still another example, the second data may mean a ratio of the reference data identified on the basis of the cardiac output and the total peripheral resistance and the first data identified on the basis of the cardiac output and the total peripheral resistance. However, an embodiment is not limited to this. In various embodiments, the second data may indicate a state of a cardiovascular load of the user. In various embodiments, because the second data indicates a relative difference between the reference data and the first data, the second data may indicate whether the cardiovascular load of the user is increased or decreased. In various embodiments, the second data may indicate what influence a circulatory system has on the user. In various embodiments, because the second data indicates the state of the cardiovascular load of the user, or indicates whether the cardiovascular load of the user has been increased or decreased, the second data may be referred as a heart load factor (HLF).

In various embodiments, the processor 120 may display an indication for indicating a health status of the user on the basis at least of the second data, by using the display 160. In various embodiments, the indication may be displayed within a user interface of an application stored in the electronic device 101 and presenting a health care service. In various embodiments, the indication may be presented in the form of notification as well. In various embodiments, the indication may be changed on the basis of an amplitude of the second data. In various embodiments, the indication may include a first track indicating the reference data, a second track indicating a plurality of candidate values for indicating the second data, and an indicator indicating, in the second track, a candidate value corresponding to the second data among the plurality of candidate values. For example, the second track may be displayed next to the first track, and the indicator may be configured with an arrow indicating the candidate value corresponding to the second data among the plurality of candidate values. In various embodiments, the first track and the second track may be configured with at least part of a ring. In various embodiments, the first track and the second track may be configured with a bar. An example of the indication will be described later through a description of FIG. 4C and FIG. 4D.

In various embodiments, the plurality of candidate values may have different distributions or ranges in the second track according to a bodily characteristic of the user. In various embodiments, at least part of sections between the plurality of candidate values in the second track may be changed according to the bodily characteristic of the user. The bodily characteristic of the user may be identified on the basis of the reference data. For example, in response to the reference data related with a blood pressure being configured with data higher than a reference blood pressure, the processor 120 may identify the bodily characteristic of the user as a high blood pressure. For another example, in response to the reference data related with a blood sugar being configured with data higher than a reference blood sugar, the processor 120 may identify the bodily characteristic of the user as diabetes. However, an embodiment is not limited to this. For example, in response to the bodily characteristic of the user being identified as a normal blood pressure, the processor 120 may configure a range of the plurality of candidate values in the second track from 1.0 to 2.0. In response to the bodily characteristic of the user being identified as a high blood pressure, the processor 120 may configure a range of the plurality of candidate values in the second track from 1.0 to 1.5. For another example, in response to the bodily characteristic of the user being identified as a normal blood pressure, the processor 120 may configure sections between the plurality of candidate values in the second track, with a first section having a range of 1.0 to 1.5 and a second section having a range of 1.5 to 2.0. In response to the bodily characteristic of the user being identified as a high blood pressure, the processor 120 may configure sections between the plurality of candidate values in the second track, with a first section having a range of 1.0 to 1.2 and a second section having a range of 1.2 to 2.0. However, an embodiment is not limited to this.

In various embodiments, the plurality of candidate values may be displayed explicitly within the indication. In various embodiments, the plurality of candidate values may be indicated indirectly on the basis of a location of the indicator in the second track, without being displayed explicitly within the indication. In various embodiments, the sections between the plurality of candidate values may be displayed explicitly within the indication. In this case, each of the sections between the plurality of candidate values may have a mutually different color according to a load degree of the heart of the user. In various embodiments, the sections between the plurality of candidate values may be indicated indirectly on the basis of a location of the indication in the second track, without being displayed explicitly within the indication. In this case, the color of the indication may be changed by the processor 120 on the basis of the location of the indicator in the second track.

In various embodiments, the processor 120 may associate information on a health status of the user and the second data.

In various embodiments, the processor 120 may display a plurality of objects, together with the indication. The plurality of objects may be used to record, in the electronic device 101, a body condition of the user during the course of obtaining the biometric information by using the at least one biometric sensor 210. Each of the plurality of objects may indicate each of a plurality of body conditions defined in the electronic device 101. For example, the plurality of body conditions may be one or more of a general state, a resting state, a before-exercise state, an after-exercise state, a tired state, an unwell state, an excited state, a surprised state, a sad state, an angry state, a fearful state, or an in-love state.

In various embodiments, the processor 120 may obtain an input for one object among the plurality of objects. In response to the obtaining, the processor 120 may map the second data to information on a body condition indicated by the one object among the plurality of body conditions. The processor 120 may store, in the memory 130, the second data mapped to the information on the body condition indicated by the one object. Because the first data or the second data is required to be classified according to the body condition of the user, the processor 120 may store, in the memory 130, the second data mapped to the information on the body condition indicated by the one object.

In various embodiments, the processor 120 may obtain information on a change of movement of the electronic device 101 by using the motion sensor 220 in a second time interval related with a first time interval during which the biometric information is obtained. For example, the second time interval may correspond to the first time interval. For another example, the second time interval may be a time interval from a first timing before (or after) a specified time interval from a start timing of the first time interval to a second timing corresponding to an end timing of the first time interval. For further example, the second time interval may be a time interval from a third timing corresponding to the start timing of the first time interval to a fourth timing before (or after) a specified time interval from the end timing of the first time interval. However, an embodiment is not limited to this. In various embodiments, to obtain the information on the body condition of the user, the processor 120 may obtain the information on the change of movement of the electronic device 101 by using the motion sensor 220 in the second time interval related with the first time interval during which the biometric information is obtained.

In various embodiments, by using not only at least one motion sensor 220 (e.g., a gesture sensor, a gyro sensor, an acceleration sensor, a grip sensor, and a proximity sensor) but also a barometer, a magnetic sensor, a color sensor, an infrared (IR) sensor, a temperature sensor, a humidity sensor, or an illumination sensor, the processor 120 may obtain the information on the body condition of the user.

For example, the processor 120 may obtain the information on the body condition of the user in the first time interval, on the basis at least of the information on the change of the movement. For another example, by using a sensor for measuring a temperature of an environment where the electronic device 101 is located, the processor 120 may obtain information on the temperature of the environment, and obtain the information on the body condition of the user, on the basis at least of the information on the temperature. For further example, the processor 120 may identify an area where the electronic device 101 is located by using a GPS, and obtain the information on the body condition of the user on the basis at least of the identification. For yet another example, the processor 120 may receive the information on the temperature of the environment from an external electronic device, and obtain the information on the body condition of the user on the basis at least of the received information as well. However, an embodiment is not limited to this.

In various embodiments, the processor 120 may map the second data to the information on the body condition. In various embodiments, the processor 120 may store, in the memory 130, the second data which has been mapped to the information on the body condition.

In various embodiments, the processor 120 may update a database for recording a health status of the user, by storing the second data in the memory 130. In various embodiments, the processor 120 may obtain information on a trend of the health status of the user on the basis of the updated database.

In various embodiments, the processor 120 may identify whether the obtained information on the trend corresponds to at least one specified condition. In various embodiments, the at least one specified condition may be configured in the electronic device 101 in order to guide to refine a health of the user. For example, the at least one specified condition may include that the information on the trend indicates a high value continuously. For another example, the at least one specified condition may include that the information on the trend indicates a relatively high value after sleep. For further example, the at least one specified condition may include that the information on the trend indicates a relatively high value after sleep. However, an embodiment is not limited to this.

In various embodiments, the processor 120 may display a notification for guiding to refine the health status of the user, based on identifying that the obtained information on the trend corresponds to the at least one specified condition. In various embodiments, the notification may be implemented in various forms. For example, the notification may include information for guiding to decrease a body weight of the user. For another example, the notification may include information for indicating that a quality of sleep of the user is equal to or is less than a reference numerical value. For further example, the notification may include information for indicating that the user needs to visit a hospital because the user suffers an apneic sleep state. In this case, the processor 120 may further display information for indicating a location of the hospital around the user within the notification. However, an embodiment is not limited to this.

In various embodiments, the notification may be displayed in various locations. For example, the notification may be displayed within a lock screen. For another example, the notification may be displayed within a wallpaper as well. For further example, the notification may be displayed within a quick menu region (e.g., notification center) which is displayed through a drag input going from an edge region of an upper end of a screen to another region or a drag input going from an edge region of a lower end of the screen to another region as well. However, an embodiment is not limited to this.

In various embodiments, the processor 120 may identify whether the second data is outside of a specified range. In various embodiments, the specified range may be configured in the electronic device 101 in order to identify whether a cardiovascular state of a user during the course of obtaining the biometric information is a resting state or is a risk state. In various embodiments, by using the display 160, the processor 120 may display a notification for guiding to refine a health status of the user, based on identifying that the second data is outside of the specified range. For example, the processor 120 may display the notification including a breathing guide for decreasing a heart rate of the user, based on identifying that the second data is outside of the specified range. For another example, the processor 120 may display the notification for guiding to stop an exercise which the user is taking, based on identifying that the second data is outside of the specified range. For further example, the processor 120 may display the notification for indicating that the user is required to perform an aerobic exercise, based on identifying that the second data is outside of the specified range. However, an embodiment is not limited to this.

In various embodiments, the processor 120 may transmit information on the second data to an external electronic device. In various embodiments, the processor 120 may transmit the information on the second data to a big data server. On the basis at least of the information on the second data, the big data server may obtain information on a health status of the user according to one or more of machine learning, a neural network, or a deep learning algorithm. The big data server may present the information on the health status to the electronic device 101. In various embodiments, the processor 120 may transmit the information on the second data to a server related with a hospital. To present the information on the second data to a specialist such as a doctor, etc., the processor 120 may transmit the information on the second data to the server related with the hospital. In various embodiments, the processor 120 may transmit the information on the second data to another electronic device 102 associated with the electronic device 101. For example, in response to the display 160 of the electronic device 101 having a restricted size, the electronic device 101 may transmit the information on the second data to the another electronic device 102, for the sake of enhancement of the visibility of the second data.

In various embodiments, the transmission of the information on the second data may be carried out on the basis of various conditions. For example, the processor 120 may identify that a specified time arrives, and transmit the information on the second data on the basis of the identification. For another example, in response to obtaining the information on the second data or as soon as obtaining the information on the second data, the processor 120 may transmit the information on the second data. For further example, in response to identifying that the electronic device 101 is located within a specified area, the processor 120 may transmit the information on the second data. For yet another example, on the basis of that data such as the second data is stored a specified capacity or more in the memory 130 of the electronic device 101, the processor 120 may transmit information on the data including the second data. However, an embodiment is not limited to this.

As described above, the electronic device 101 of various embodiments may present a service of monitoring a cardiovascular state of a user, by obtaining the second data indicating a relative difference between the reference data and the first data, and performing various processes (e.g., displaying of an indication, transmitting of information on the second data, storing of the information on the second data, etc.) using the second data. The electronic device 101 of various embodiments may present guidance information on the health status of the user, on the basis of the monitoring result.

Figure 3:
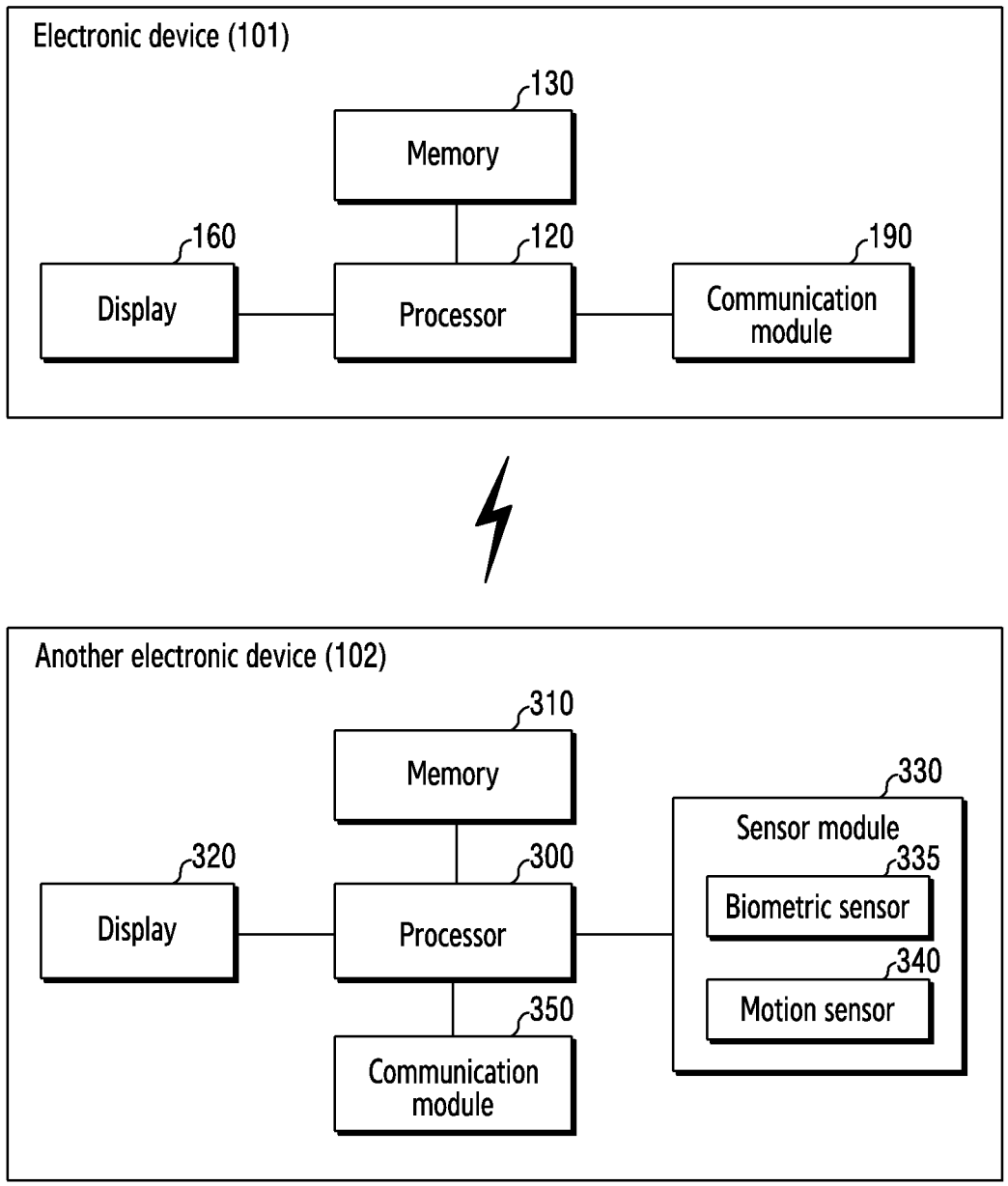
FIG. 3 illustrates an example of functional constructions of an electronic device and another electronic device according to various embodiments.

FIG. 3 illustrates an example of functional constructions of an electronic device and another electronic device according to various embodiments. This functional construction may be included in at least one of the electronic device 101 shown in FIG. 1, the electronic device 101 shown in FIG. 2, or the electronic device 102 shown in FIG. 1.

Referring to FIG. 3, the electronic device 101 may include a processor 120, a memory 130, a display 160, and a communication module 190.

In various embodiments, the processor 120 may include the processor 120 shown in FIG. 1 or FIG. 2, and the memory 130 may include the memory 130 shown in FIG. 1 or FIG. 2, and the display 160 may include the display device 160 shown in FIG. 1 or FIG. 2, and the communication module 190 may include at least one of the communication module 190 shown in FIG. 1 or FIG. 2 or the interface 177 shown in FIG. 1.

Referring to FIG. 3, the another electronic device 102 may be an electronic device for obtaining biometric information of a user related with the electronic device 101, or obtaining the first data described through FIG. 2, or obtaining the second data described through FIG. 2. The another electronic device 102 may present the biometric information, the first data, or the second data to the electronic device 102. The biometric information, the first data, or the second data presented to the electronic device 101 may be processed by the electronic device 101. In various embodiments, the another electronic device 102 may be worn by the user related with the electronic device 101 for the sake of obtaining of the biometric information, the first data, or the second data. In various embodiments, the another electronic device 102 may operate on the basis of a user account corresponding to a user account of the electronic device 101, for the sake of association (e.g., the presenting of the biometric information, the first data, or the second data) with the electronic device 101.

In various embodiments, the another electronic device 102 may include a processor 300, a memory 310, a display 320, a sensor module 330, a biometric sensor 335 included in the sensor module 330, a motion sensor 340 included in the sensor module 330, and a communication module 350.

In various embodiments, the processor 300 may include the processor 120 shown in FIG. 1 or FIG. 2, and the memory 310 may include the memory 130 shown in FIG. 1 or FIG. 2, and the display 320 may include the display device 160 shown in FIG. 1 or FIG. 2, and the sensor module 330 may include the sensor module 176 shown in FIG. 1 or FIG. 2, and the communication module 350 may include at least one of the communication module 190 shown in FIG. 1 or FIG. 2 or the interface 177 shown in FIG. 1.

In various embodiments, the processor 300 may obtain body information of a user by using the biometric sensor 335. In various embodiments, the processor 300 may transmit biometric information of the user to the electronic device 101 by using the communication module 350. In various embodiments, the biometric information may correspond to biometric information described through FIG. 2. In various embodiments, the processor 120 of the electronic device 101 may obtain first data indicating a cardiovascular state of the user from the biometric information. In various embodiments, the first data may correspond to the first data described through FIG. 2. In various embodiments, the processor 120 of the electronic device 101 may obtain second data indicating a relative difference between the first data and the reference data. In various embodiments, the reference data may correspond to the reference data described through FIG. 2. In various embodiments, the second data may correspond to the second data described through FIG. 2. In various embodiments, the processor 120 of the electronic device 101 may process the second data through various methods. For example, the processor 120 may obtain an input for executing an application presenting a service related with health stored in the electronic device 101, and display, through the display 160, the indication for indicating a health status of the user by using the second data on the basis of the obtaining.

In various embodiments, the processor 300 may obtain the body information of the user, and obtain the first data indicating the cardiovascular state of the user on the basis of the obtained body information, and transmit information on the first data to the electronic device 101. In various embodiments, the processor 120 may obtain the second data indicating the relative difference between the first data and the second data, and process the obtained second data through various methods.

In various embodiments, the processor 300 may obtain the body information of the user, and obtain the first data from the obtained body information, and obtain the second data indicating the relative difference between the first data and the reference data. The processor 300 may transmit the information on the second data to the electronic device 101. The processor 120 may process the received information on the second data through various methods.

In various embodiments, the processor 300 may selectively perform the transmitting of the biometric information, the transmitting of the first data, or the transmitting of the second data according to a state of the another electronic device 102 as well. For example, in response to a remaining capacity of a battery of the another electronic device 102 being less than a first threshold, the processor 300 may transmit the biometric information in order to decrease a power consumption of the another electronic device 102. In response to the remaining capacity of the battery of the another electronic device 102 being between the first threshold and a second threshold, the processor 300 may obtain the first data from the biometric information and transmit the first data. In response to the remaining capacity of the battery of the another electronic device 102 being greater than the second threshold, the processor 300 may obtain the first data from the biometric information, and obtain the second data on the basis of the first data, and then transmit the information on the second data to the electronic device 101. However, an embodiment is not limited to this.

In various embodiments, the processor 300 may obtain information on a change of movement of the another electronic device 102 by using the motion sensor 220 in a second time interval related with a first time interval during which the biometric information is obtained. In various embodiments, the processor 300 may transmit the information on the change of the movement of the another electronic device 102, to the electronic device 101. On the basis at least of the received information, the processor 120 may obtain information on a body condition of the user in the first time interval, and map the second data to the information on the body condition, and process the second data which has been mapped to the information on the body condition. In various embodiments, the processor 300 may obtain the information on the body condition of the user in the first time interval on the basis at least of the information on the change of the movement, and transmit the information on the body condition of the user to the electronic device 101. The processor 120 may map the second data to the received information on the body condition of the user, and process the second data which has been mapped to the information on the body condition.

In various embodiments, the information on the change of the movement of the another electronic device 102 or the information on the body condition may be transmitted together with the second data as well, and may be transmitted at a different time point distinct from a time point of transmission of the second data as well.

In various embodiments, on the basis of the remaining capacity of the battery of the another electronic device 102, the processor 300 may change a communication technique which is used to transmit the information. For example, in response to the remaining capacity of the battery of the another electronic device 102 being less than a threshold, the processor 300 may transmit the information, on the basis of a first communication technique (e.g., Bluetooth) having a lower data rate than a second communication technique (e.g. Wi-Fi direct) but consuming smaller power than the second communication technique. In response to the remaining capacity of the battery of the another electronic device 102 being equal to or being greater than the threshold, the processor 300 may transmit the information, on the basis of the second communication technique (e.g., Wi-Fi direct) having a higher data rate than the first communication technique (e.g., Bluetooth) but consuming greater power than the first communication technique. However, an embodiment is not limited to this.

As described above, the electronic device 101 of various embodiments may not only decrease the number of operations of the electronic device 101 but also obtain more accurate data, by obtaining the biometric information of the user by using the another electronic device 102 worn by the user related with the electronic device 101.

An electronic device (e.g., the electronic device 101) of various embodiments described above may include a housing, a display (e.g., the display device 160) exposed through a first portion of the housing, a photoplethysmogram (PPG) sensor (e.g., the sensor module 176) exposed through a second portion of the housing, a processor (e.g., the processor 120) located in the housing and operatively connected with the display and the PPG sensor, a memory (e.g., the memory 130) located in the housing and operatively connected with the processor. The memory may store instructions of, at execution, allowing the processor to, in a first operation, receive first data by using the PPG sensor and determine a plurality of reference ranges of a blood pressure on the basis at least in part of the first data, and store the plurality of reference ranges, and in a second operation, after the first operation, receive second data by using the PPG sensor, and select one reference range among the plurality of reference ranges on the basis at least in part of the second data, and present at least one of a graphical user interface (GUI), a text, or a numerical value in order to indicate the selected reference range among the plurality of reference ranges on the display.

In various embodiments, the instructions may allow the processor to determine the plurality of ranges on the basis at least of pulse wave analysis (PWA) for the first data. In various embodiments, the instructions may allow the processor to use at least one of a systolic blood pressure (SBP) value, a diastolic blood pressure (DBP) value, a mean arterial pressure (MAP) value, a cardiac output (CO) value, a total peripheral resistance (TPR), or a resting heart rate (RHR) within the PWA.

In various embodiments, the instructions may allow the processor to present a user guide on the display in the first operation before receiving the first data.

An electronic device (e.g., the electronic device 101) of various embodiments described above may include a memory (e.g., the memory 130) storing instructions, at least one biometric sensor (e.g., the at least one biometric sensor 210), a display (e.g., the display 160), and at least one processor (e.g., the processor 120). The at least one processor may be configured to execute the stored instructions in order to obtain biometric information of a user related with the electronic device by using the at least one biometric sensor, obtain first data indicating a cardiovascular state of the user from the biometric information, obtain second data indicating a relative difference between the first data and reference data indicating a cardiovascular state in a resting state of the user, and display, by using the display, an indication for indicating a health status of the user, on the basis at least of the second data.

In various embodiments, the at least one processor may be further configured to execute the stored instructions in order to display guidance information for guiding a state of the user to the resting state, by using the display, and after displaying the guidance information, obtain another biometric information of the user by using the at least one biometric sensor, and store, as the reference data, data indicating a cardiovascular state of the user obtained from the another biometric information.

In various embodiments, the electronic device may further include a communication module (e.g., the communication module 190), and the at least one processor may be further configured to execute the stored instructions in order to receive the reference data from an external electronic device by using the communication module.

In various embodiments, the at least one processor may be configured to execute the stored instructions in order to display the indication which includes a first track indicating the reference data, a second track indicating a plurality of candidate values for indicating the second data, and an indicator indicating, in the second track, a candidate value corresponding to the second data among the plurality of candidate values, on the basis at least of the second data. For example, the second track may be displayed next to the first rack, and the indicator may be configured with an arrow indicating the candidate value corresponding to the second data among the plurality of candidate values. For example, the first track and the second track may be configured with at least part of a ring. For another example, the first track and the second track may be configured with a bar.

In various embodiments, the at least one processor may be configured to execute the stored instructions in order to display a plurality of objects for recording, in the electronic device, a body condition of the user during the course of obtaining the biometric information by using the at least one biometric sensor, together with the indication. Each of the plurality of objects may indicate each of a plurality of body conditions defined in the electronic device. In various embodiments, the at least one processor may be further configured to execute the stored instructions in order to obtain an input for a first object among the plurality of objects, and in response to the obtaining, map the second data to information on a body condition indicated by the first object among the plurality of body conditions, and store, in the memory, the second data mapped to the information on the body condition. In various embodiments, the at least one processor may be further configured to execute the stored instructions in order to update a database for recording a health status of the user, on the basis of the second data mapped to the information on the body condition, obtain information on a trend of the health status of the user, on the basis of the updated database, and display a notification for guiding to refine the health status of the user, on the basis of that the obtained information on the trend corresponds to at least one specified condition.

In various embodiments, the electronic device may further include at least one sensor distinct from the at least one biometric sensor, and the at least one processor may be further configured to execute the stored instructions in order to obtain information on a change of movement of the electronic device, by using the at least one sensor, within a second time interval related with a first time interval during which the biometric information is obtained, obtain information on a body condition of the user in the first time interval, on the basis at least of the information on the change of the movement of the electronic device, map the second data to the information on the body condition, and store, in the memory, the second data mapped to the information on the body condition. In various embodiments, the at least one processor may be further configured to execute the stored instructions in order to update a database for recording the health status of the user, on the basis of the second data mapped to the information on the body condition, obtain information on a trend of the health status of the user, on the basis of the updated database, and display a notification for guiding to refine the health status of the user, on the basis of that the obtained information on the trend corresponds to at least one specified condition.

In various embodiments, the at least one processor may be further configured to execute the stored instructions in order to identify that the second data is outside of a specified range, and in response to the identification, display a notification for guiding to refine the health status of the user.

An electronic device of various embodiments described above may include a memory storing instructions, a communication module, a display, and at least one processor. The at least one processor may be configured to execute the stored instructions in order to obtain first data indicating a cardiovascular state of a user which has been obtained on the basis of biometric information of the user obtained through at least one biometric sensor of another electronic device, from the another electronic device interworking with the electronic device and worn by the user related with the electronic device, obtain second data indicating a relative difference between the first data and reference data indicating a cardiovascular state in a resting state of the user, obtain an input for executing an application presenting a service related with a health stored in the electronic device, and display, through the display, an indication for indicating the health status of the user, by using the second data, on the basis of the obtaining.

In various embodiments, the at least one biometric sensor of the another electronic device may be exposed through at least part of a housing of the another electronic device, in order to get in contact with at least part of a body of the user.

In various embodiments, the at least one processor may be further configured to execute the stored instructions in order to receive information on a change of movement of the another electronic device obtained through at least one sensor of the another electronic device within a second time interval related with a first time interval during the course of obtaining the biometric information, from the another electronic device, and obtain information on a body condition of the user within the first time interval, on the basis at least of the information of the change of the movement of the another electronic device, and map the second data to information on the body condition, and store the second data mapped to the information on the body condition in the memory.

In various embodiments, the at least one processor may be further configured to execute the stored instructions in order to receive information of a body condition of the user during the course of obtaining the biometric information, from the another electronic device, map the second data to the information on the body condition, and store the second data mapped to the information on the body condition in the memory. The information on the body condition may be obtained by the another electronic device, on the basis of the information on a change of movement of the another electronic device which has been obtained through at least one sensor of the another electronic device within a second time interval related with a first time interval during the course of obtaining the biometric information.

In various embodiments, a user account of the electronic device may correspond to a user account of the another electronic device.

An electronic device of various embodiments described above may include a memory storing instructions, at least one biometric sensor, a display, and at least one processor. The at least one processor may be configured to execute the stored instructions in order to obtain data indicating a cardiovascular state of a user related with the electronic device by using the at least one biometric sensor, identify that a relative difference between the data and reference data indicating a cardiovascular state in a resting state of the user is changed, and change at least part of an indication indicating the relative difference indicated using the display, on the basis of the identification.

Figure 4A:
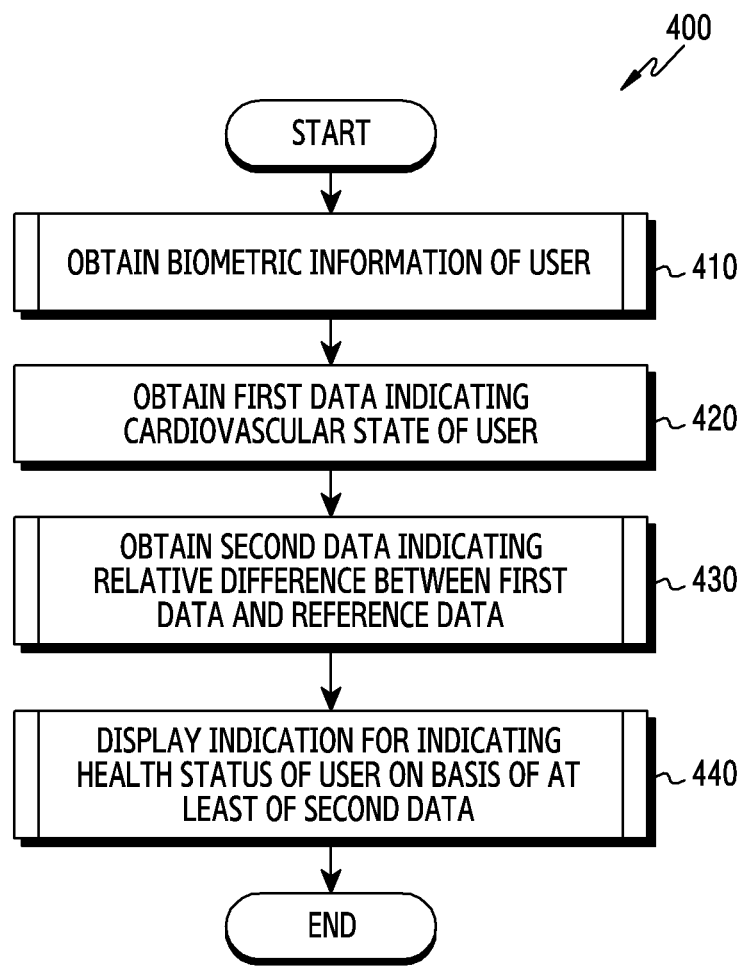
FIG. 4A illustrates an example of an operation of an electronic device according to various embodiments.

FIG. 4A illustrates an example of an operation of an electronic device according to various embodiments. This operation (e.g., operation 400) may be performed by the electronic device 101 shown in FIG. 1, FIG. 2 or FIG. 3, or the processor 120 of the electronic device 101.

Figure 4B:
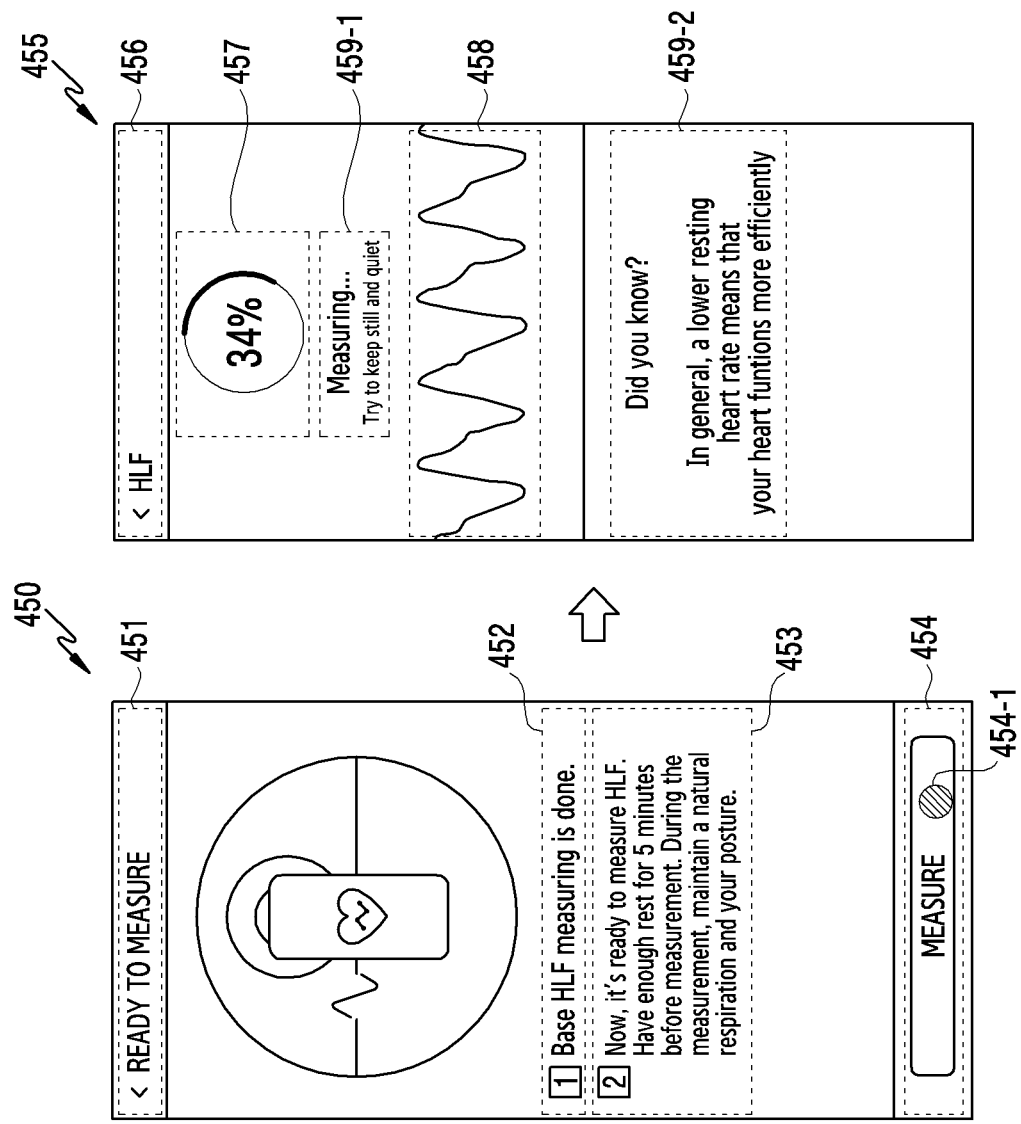
FIG. 4B illustrates an example of a user interface displayed in an electronic device according to various embodiments.
Figure 4C:
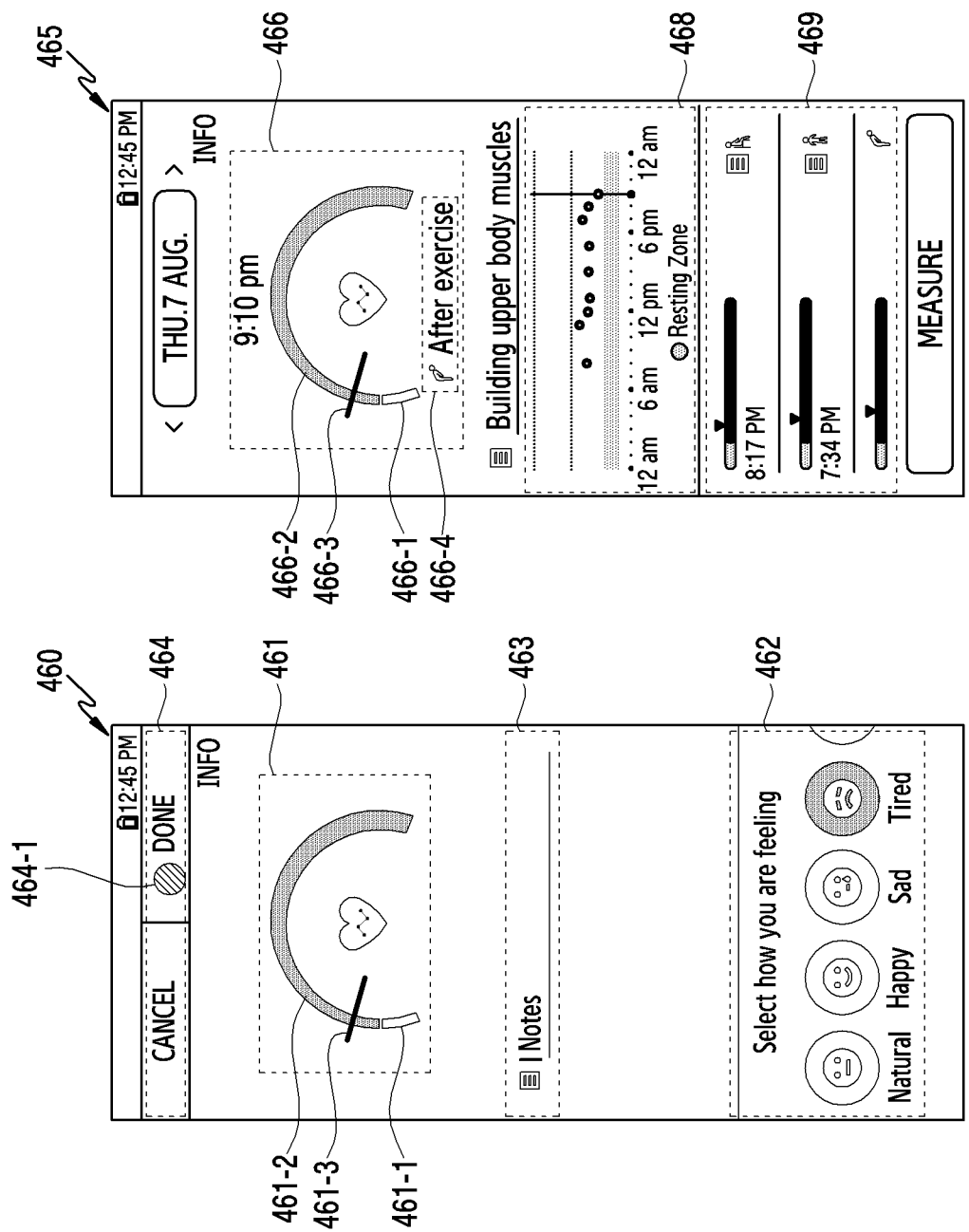
FIG. 4C illustrates another example of a user interface displayed in an electronic device according to various embodiments.
Figure 4D:
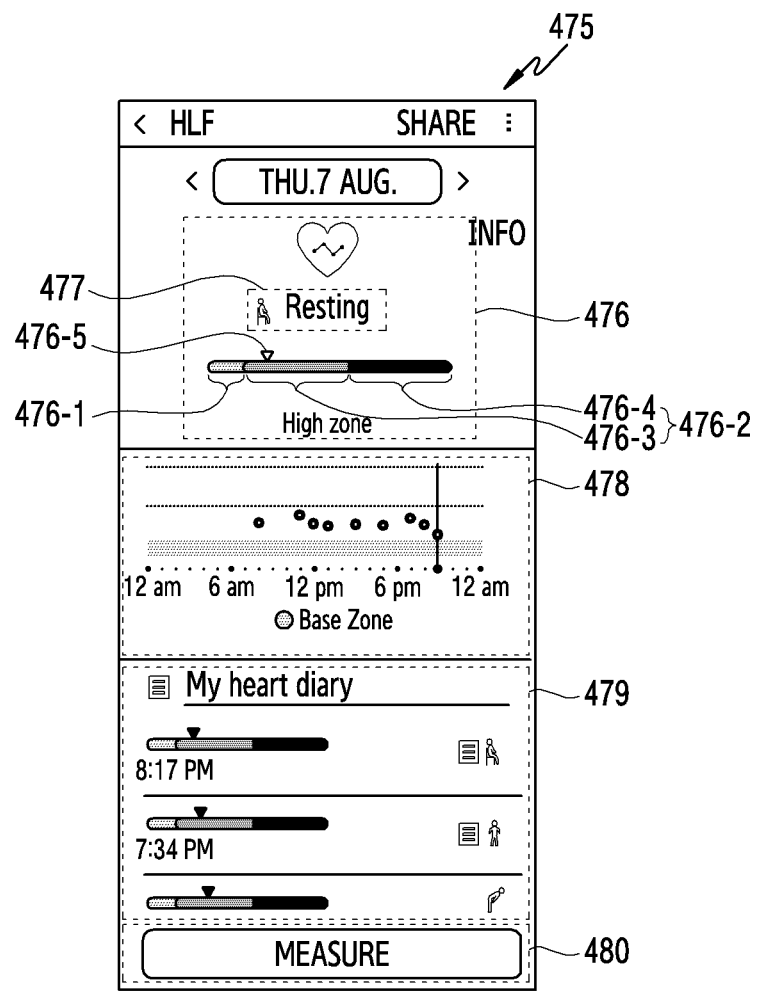
FIG. 4D illustrates a further example of a user interface displayed in an electronic device according to various embodiments.
Figure 4E:
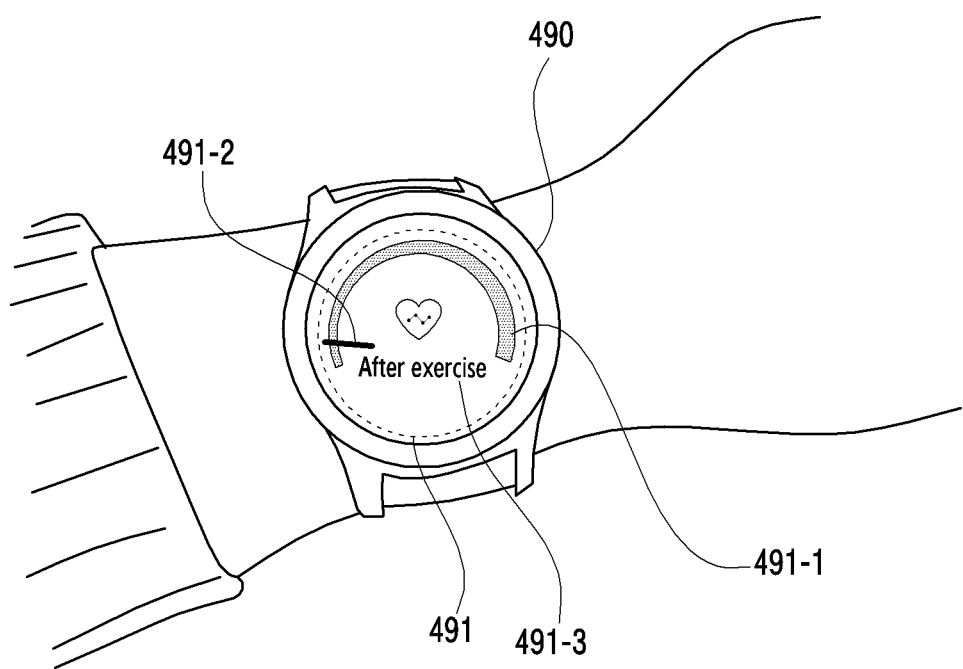
FIG. 4E illustrates a yet another example of a user interface displayed in an electronic device according to various embodiments.

FIG. 4B illustrates an example of a user interface displayed in an electronic device according to various embodiments. FIG. 4C illustrates another example of a user interface displayed in an electronic device according to various embodiments. FIG. 4D illustrates a further example of a user interface displayed in an electronic device according to various embodiments. FIG. 4E illustrates a yet another example of a user interface displayed in an electronic device according to various embodiments.

Referring to FIG. 4A, in operation 410, the processor 120 may obtain biometric information of a user. In various embodiments, the biometric information may correspond to the biometric information described through FIG. 2. In various embodiments, the processor 120 may obtain the biometric information of the user related with the electronic device 101 by using the at least one biometric sensor 210. In various embodiments, to obtain the biometric information by using the at least one biometric sensor 210, the processor 120 may display information by using the display 160. In various embodiments, the information may be displayed within a user interface of an application presenting a service related with health. For example, referring to FIG. 4B, the processor 120 may display a user interface 450, for the sake of obtaining of the biometric information. In various embodiments, the user interface 450 may include a region 451 for indicating a current step among a plurality of steps required for obtaining of biometric information, information 452 for indicating that it is a state in which the reference data has been obtained before the current step, information 453 including guidance information for obtaining of the biometric information, and an object 454 for initiating the obtaining of the biometric information. In various embodiments, the processor 120 may obtain an input 454-1 for the object 454. For example, the input 454-1 may be a touch input for the object 454.

In various embodiments, in response to obtaining of the input 454-1, the processor 120 may activate the at least one biometric sensor 210. In various embodiments, in response to the obtaining of the input 454-1, the processor 120 may display the user interface 455 changed from the user interface 450 by using the display 160. In various embodiments, the user interface 455 may include a region 456 for indicating a current step among a plurality of steps required for obtaining of biometric information, a progress bar 457 for indicating a degree in which the biometric information has been obtained by using the activated at least one biometric sensor 210, a wave form 458 identified from the biometric information which is being obtained, information 459-1 for guiding a posture of the user while the biometric information is obtained, and health information 459-2 related with a cardiovascular state. In various embodiments, in response to identifying that obtaining of the biometric information is completed, the processor 120 may display a user interface (e.g., the user interface 460 of FIG. 4C, the user interface 465 of FIG. 4C, etc.) changed from the user interface 455, through the display 160.

In operation 420, on the basis of the biometric information, the processor 120 may obtain first data indicating a cardiovascular state of the user. In various embodiments, the first data may correspond to the first data described through FIG. 2. In various embodiments, the processor 120 may obtain the first data from the biometric information on the basis of analysis of the biometric information. For example, the processor 120 may obtain the first data on the basis of pulse wave analysis (PWA) of the biometric information. In various embodiments, the first data may be obtained on the basis at least of factors related with a resting state obtained from a pulse wave. In various embodiments, the resting state may correspond to the restring state described through FIG. 2. In various embodiments, the factors may include at least one of a systolic blood pressure of the resting state, a diastolic blood pressure of the resting state, a mean blood pressure of the resting state, a cardiac output of the resting state, or a blood vessel total peripheral resistance of the resting state.

In various embodiments, in response to the obtained first data being outside of the reference range, the processor 120 may guide to again obtain the first data by presenting a notification or alarm.

In operation 430, the processor 120 may obtain second data indicating a relative difference between the first data and the reference data. In various embodiments, the second data may correspond to the second data described through FIG. 2. In various embodiments, the processor 120 may obtain the second data corresponding to a variation of the factors related with the first data.

In operation 440, on the basis at least of the second data, the processor 120 may display an indication for indicating a health status of the user. In various embodiments, the indication may be displayed within a user interface of an application presenting a service related with health. For example, referring to FIG. 4C, the processor 120 may display the user interface 460. In various embodiments, the user interface 460 may include an indication 461. The indication 461 may include a first track 461-1 for indicating the reference data, a second track 461-2 extended from the first track and for indicating a plurality of candidate values, and an indicator 461-3 related with the second track 461-2 and for indicating a candidate value corresponding to the second data among the plurality of candidate values. In various embodiments, an orientation of the indicator 461-3 may be changed according to an amplitude of the second data. In various embodiments, by changing the orientation of the indicator 461-3 according to the amplitude of the second data, the processor 120 may present information on a cardiovascular state of the user.

In various embodiments, to map the second data to information on a body condition of a user, the user interface 460 may further include a plurality of objects 462 for indicating a plurality of body conditions. Each of the plurality of objects 462 may indicate each of the plurality of body conditions defined in the electronic device 101. For example, the plurality of body conditions 462 may be one or more of a general state, a resting state, a before-exercise state, an after-exercise state, a tired state, an unwell state, an excited state, a surprised state, a sad state, an angry state, a fearful state, or an in-love state. In various embodiments, the processor 120 may obtain an input for one object among the plurality of objects 462. In response to the obtaining, the processor 120 may map the second data to information on a body condition, which is indicated by the one object, among the plurality of body conditions. The processor 120 may process the second data mapped to the information on the body condition which is indicated by the one object.

In various embodiments, the user interface 460 may further include a text input portion 463 for further inputting additional information related with the biometric information.

In various embodiments, the user interface 460 may further include icons 464 for inquiring whether to manage (or discard (cancel a management on)) the second data.

In various embodiments, the processor 120 may obtain an input 464-1 for an icon, which indicates managing the second data, among the icons 464. In various embodiments, in response to obtaining of the input 464-1, the processor 120 may display a user interface 465 changed from the user interface 460. In various embodiments, the user interface 465 may include an indication 466. The indication 466 may include a first track 466-1 indicating the reference data and corresponding to the first track 461-1, a second track 466-2 extended from the first track 466-1 and indicating a plurality of candidate values, and corresponding to the second track 461-2, an indicator 466-3 indicating a candidate value corresponding to the second data among the plurality of candidate values and corresponding to the indicator 461-3, and a body condition 466-4 inputted in the user interface 460 among the plurality of body conditions 462. In various embodiments, the body condition 466-4 may be inputted on the basis of information on a change of movement of the electronic device 101 or information on a change of movement of the another electronic device 102 as well.

In various embodiments, the user interface 465 may further include another indication 468 for indicating a trend of a cardiovascular state of the user during a specified time interval. In various embodiments, the another indication 468 may further include an indicator which indicates information on a time of obtaining of the biometric information, information (resting zone) on the reference data, information on an amplitude of the data for each obtaining time, and a current obtaining time. However, an embodiment is not limited to this.

In various embodiments, the user interface 465 may further include detailed information 469 on the another indication 468. The detailed information 469 may be displayed in the form of a directory or list.

FIG. 4C illustrates an example in which the second track 461-2 is displayed with one color, but this is for description convenience. In various embodiments, the second track 461-2 may be divided into a plurality of intervals, and the plurality of intervals may have mutually different colors. For example, a color of an interval spaced apart away from the first track 461-1 among the plurality of intervals may be distinct from a color of an interval adjacent to the first track 461-1. However, an embodiment is not limited to this.

Also, FIG. 4C illustrates an example of, after displaying the user interface 460, displaying the user interface 465 on the basis of a user input, but the processor 120 may directly display the user interface 465 by jumping or bypassing the displaying of the user interface 460 as well.

For another example, referring to FIG. 4D, the processor 120 may display a user interface 475 which is distinct from the user interface 460 and the user interface 465. In various embodiments, the user interface 475 may include an indication 476. The indication 476 may include a first track 476-1 for indicating the reference data, a second track 476-2 for indicating the plurality of candidate values next to the first track 476-1, and an indicator 476-5 related with the second track 476-2 and for indicating a candidate value corresponding to the second data among the plurality of candidate values. In various embodiments, a location of the indicator 476-5 may be changed according to an amplitude of the second data. In various embodiments, by changing the location of the indicator 476-5 according to the amplitude of the second data, the processor 120 may present information on a cardiovascular state of the user. In various embodiments, the processor 120 may display not only the indication 461 and the indication 466 including a track of a curved form but also the indication 476 including a track of a bar form. However, an embodiment is not limited to this.

In various embodiments, the second track 476-2 may further include a plurality of intervals according to a cardiovascular state of a user. For example, the second track 476-2 may include a sub track 476-3 for indicating that the cardiovascular state of the user corresponds to a caution state (e.g., high zone) and a sub track 476-4 for indicating that the cardiovascular state of the user corresponds to a warning state (e.g., very high zone). A boundary between the sub track 476-3 and the sub track 476-4 may be displayed differently according to a preset cardiovascular state (e.g., a normal state, a high blood pressure caution state (i.e., a high blood pressure former step), a high blood pressure state, etc.) of the user. For example, in response to the cardiovascular state of the user corresponding to the normal state, a ratio of a length of the sub track 476-3 and a length of the sub track 476-4 may be 7 to 3. For another example, in response to the cardiovascular state of the user corresponding to the high blood pressure caution state, the ratio of the length of the sub track 476-3 and the length of the sub track 476-4 may be 5 to 5. For further example, in response to the cardiovascular state of the user corresponding to the high blood pressure state, the ratio of the length of the sub track 476-3 and the length of the sub track 476-4 may be 3 to 7.

In various embodiments, the user interface 475 may further include information 477 for indicating a body condition of the user during the course of obtaining the biometric information. In various embodiments, the information 477 may be determined through an input for one object among the plurality of objects 462 shown in FIG. 4C. In various embodiments, the information 477 may be determined on the basis of information on a change of movement of the electronic device 101 or information on a change of movement of the another electronic device 102 as well.

In various embodiments, the user interface 475 may further include another indication 478 for indicating a trend of a cardiovascular state of the user during a specified time interval. In various embodiments, the another indication 478 may include an indicator indicating information on a time of obtaining of the biometric information, information (base zone) on the reference data, information on an amplitude of the data for each obtaining time, and a current obtaining time. However, an embodiment is not limited to this.

In various embodiments, the user interface 475 may further include detailed information 479 on the another indication 478. The detailed information 479 may be displayed in the form of a directory or list.

In various embodiments, the user interface 475 may further include an icon 480 for performing the obtaining of the biometric information.

For further example, referring to FIG. 4E, in response to the electronic device 101 being a wearable device (e.g., a smart watch), the processor 120 may display a user interface 490. In various embodiments, because the user interface 490 is displayed in the smart watch having a display of more restricted size than a smart phone, the user interface 490 may display optimal or reduced information in comparison with the user interface 460, the user interface 465, and the user interface 475. In various embodiments, the user interface 490 may include an indication 491. The indication 491 may include a track 491-1 for indicating a plurality of candidate values, an indicator 491-2 for indicating a candidate value corresponding to the second data among the plurality of candidate values, and information 491-3 for indicating a state of a user during the course of obtaining the second data. A color of the track 491-1 may be configured on the basis of a difference with the reference data. For example, a color of a region of the track 491-1 where the difference with the reference data is relatively small may be different from a color of a region of the track 491-1 where the difference with the reference data is relatively large.

As described above, by displaying an indication which indicates a cardiovascular health status of the user, the electronic device 101 of various embodiments may intuitively guide whether there is a need for the refinement of the cardiovascular health status of the user.

Figure 5A:
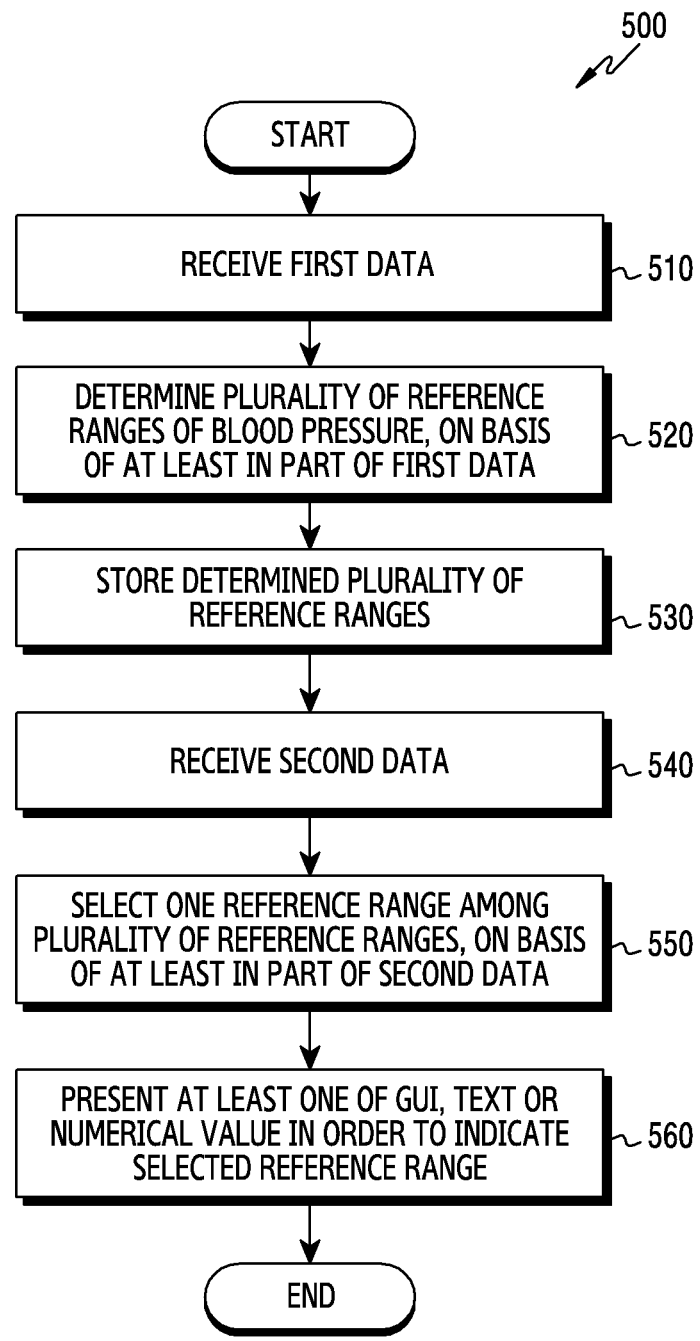
FIG. 5A illustrates another example of an operation of an electronic device according to various embodiments.

FIG. 5A illustrates another example of an operation of an electronic device according to various embodiments. This operation (e.g., operation 500) may be performed by the electronic device 101 shown in FIG. 1, FIG. 2 or FIG. 3, or the processor 120 of the electronic device 101.

Referring to FIG. 5A, in operation 510, the processor 120 may receive first data through a photoplethysmogram (PPG) sensor. In various embodiments, the PPG sensor may be exposed through a second portion of a housing of the electronic device 101 distinct from a first portion of the housing of the electronic device 101 through which the display 160 of the electronic device 101 has been exposed. In various embodiments, the first data may indicate a cardiovascular state of a resting state of a user. In various embodiments, the first data may correspond to the first data described through FIG. 2. In various embodiments, before receiving the first data, the processor 120 may present a user guide through the display 160.

In operation 520, the processor 120 may determine a plurality of reference ranges of a blood pressure, on the basis at least in part of the first data. In various embodiments, the plurality of reference ranges may mean a plurality of ranges which divide values indicating the cardiovascular state of the user. In various embodiments, the plurality of reference ranges may correspond to the plurality of candidate values described through FIG. 4A. In various embodiments, the plurality of reference ranges may be configured differently according to the first data indicating the cardiovascular state of the resting state of the user. In various embodiments, by performing pulse wave analysis (PWA) for the first data, the processor 120 may determine the plurality of ranges. In various embodiments, the pulse wave analysis may include at least one of obtaining a systolic blood pressure value from a pulse wave indicating the first data, obtaining a diastolic blood pressure value from the pulse wave indicating the first data, or obtaining a mean blood pressure value from the pulse wave indicating the first data.

In operation 530, the processor 120 may store the determined plurality of reference ranges. In various embodiments, the processor 120 may store the plurality of reference ranges, in order to determine a reference range corresponding to second data to be received afterward (described later through operation 540) among the plurality of reference ranges. In various embodiments, the processor 120 may store the plurality of reference ranges, in order to display the plurality of reference ranges through the display 160 together with the determined reference range.

In various embodiments, operation 510 to operation 530 may be united and referred to as a first operation, in aspect of obtaining the data indicating the cardiovascular state of the resting state of the user.

In operation 540, after the first operation, the processor 120 may receive the second data by using the PPG sensor.

In operation 550, the processor 120 may select one reference range among the plurality of reference ranges, on the basis at least in part of the second data. For example, the processor 120 may identify one reference range including the second data among the plurality of reference ranges.

In operation 560, the processor 120 may present, through the display 160, at least one of a GUI, a text, or a numeric value, in order to indicate the selected reference range among the plurality of reference ranges. For example, the processor 120 may display the user interface 460 or the user interface 465 of FIG. 4C, the user interface 475 of FIG. 4D, or the user interface 490 of FIG. 4E through the display 160.

Figure 5B:
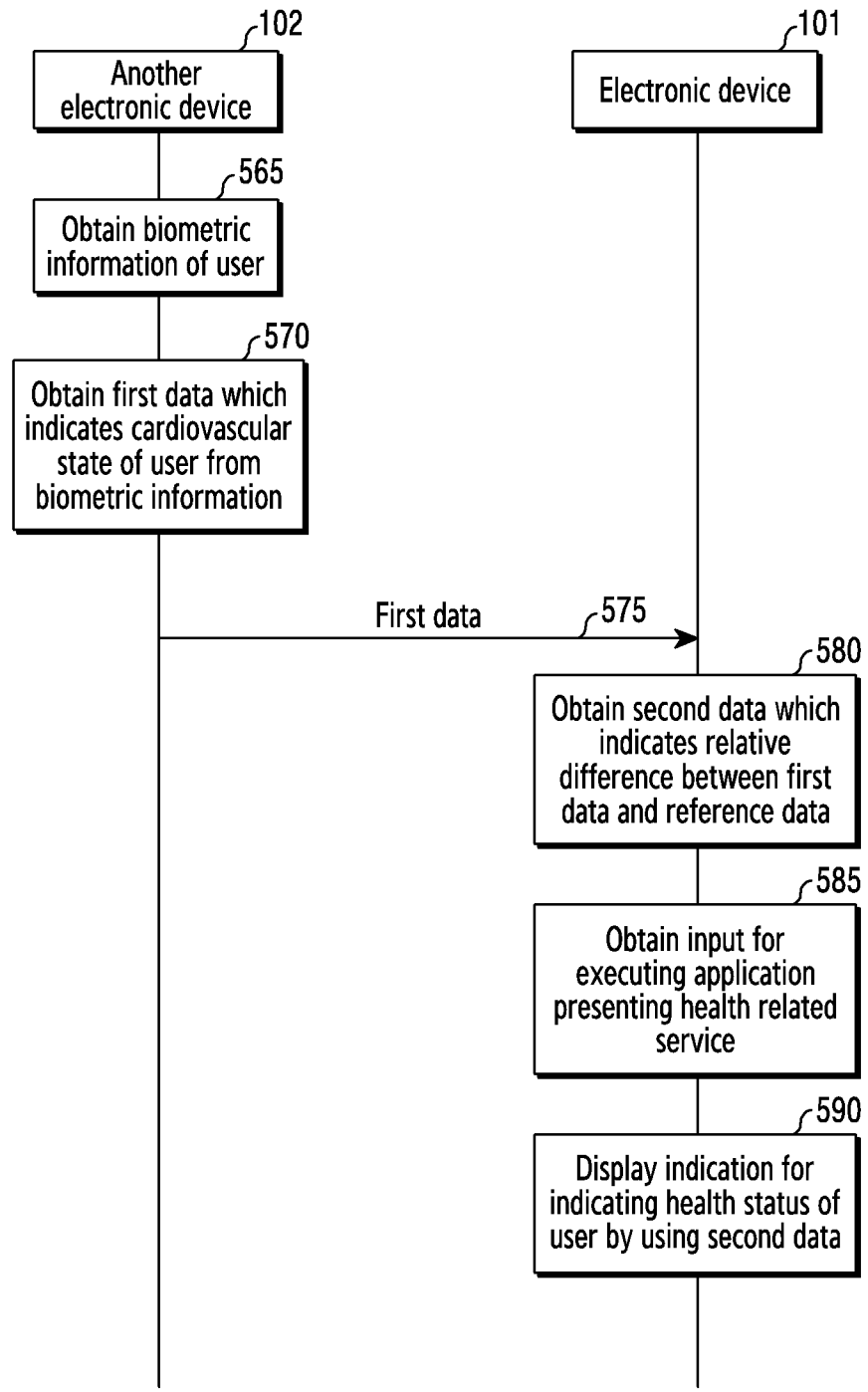
FIG. 5B illustrates an example of an operation of an electronic device and another electronic device according to various embodiments.

FIG. 5B illustrates an example of an operation of an electronic device and another electronic device according to various embodiments. This operation may be performed by the electronic device 101 shown in FIG. 1, FIG. 2 or FIG. 3 or the processor 120 of the electronic device 101, and the electronic device 102 shown in FIG. 1 or FIG. 3 or the processor 300 of the electronic device 102.

Referring to FIG. 5B, in operation 565, the another electronic device 102 may obtain biometric information of a user. In various embodiments, the another electronic device 102 worn by a user related with the electronic device 101 may obtain the biometric information of the user, by using the at least one biometric sensor 335 which has been exposed through at least part of the housing of the another electronic device 102 and has got in contact with at least part of a body of the user.

In operation 570, the another electronic device 102 may obtain first data indicating a cardiovascular state of the user from the biometric information. In various embodiments, the first data may correspond to the first data described through FIG. 2. Operation 570 may be performed identically or similarly with operation 420 of FIG. 4A.

In operation 575, the another electronic device 102 may transmit the first data to the electronic device 101. In various embodiments, the another electronic device 102 may obtain the first data in a state of establishing connection with the electronic device 101. In this case, the another electronic device 102 may transmit the obtained first data to the electronic device 101 by using the established connection. In various embodiments, the another electronic device 102 may obtain the first data in a state of not establishing the connection with the electronic device 101. In this case, the another electronic device 102 may establish connection with the electronic device 101 on the basis of obtaining the first data. The another electronic device 102 may transmit the first data of the user to the electronic device 101 on the basis of establishing the connection. The electronic device 101 may receive the first data of the user from the another electronic device 102. For example, the another electronic device 102 may transmit the first data to the electronic device 101 in order to synchronize the first data with the electronic device 101.

In operation 580, the electronic device 101 may obtain second data which indicates a relative difference between the first data and the reference data. In various embodiments, the reference data may correspond to the reference data described through FIG. 2, and the second data may correspond to the second data described through FIG. 2. In various embodiments, the reference data may be obtained through at least one biometric sensor 210 of the electronic device 101. In various embodiments, operation 580 may correspond to operation 430 of FIG. 4A.

In operation 585, the electronic device 101 may obtain an input for executing an application presenting a service related with health. For example, the electronic device 101 may obtain an input for an icon for indicating the application.

In operation 590, on the basis of the obtaining, the electronic device 101 may display an indication for indicating a health status of the user, through the display 160, by using the second data. Operation 590 may correspond to operation 440 of FIG. 4A.

Though not illustrated in FIG. 5B, the electronic device 101 may transmit the second data to the another electronic device 102 in order to synchronize the second data with the another electronic device 102. The transmitting of the second data may be performed periodically as well, and may be performed on the basis of execution of the application related with health as in operation 585.

As described above, the electronic device 101 of various embodiments may obtain the data indicating the cardiovascular state of the user, by using at least one biometric sensor 335 included in the another electronic device 102, not the at least one biometric sensor 210 included in the electronic device 101, and present the indication on the basis at least of the obtained data. By presenting notification or guidance information to the user through the presenting of the indication, the electronic device 101 may increase a convenience of the user.

Figure 6:
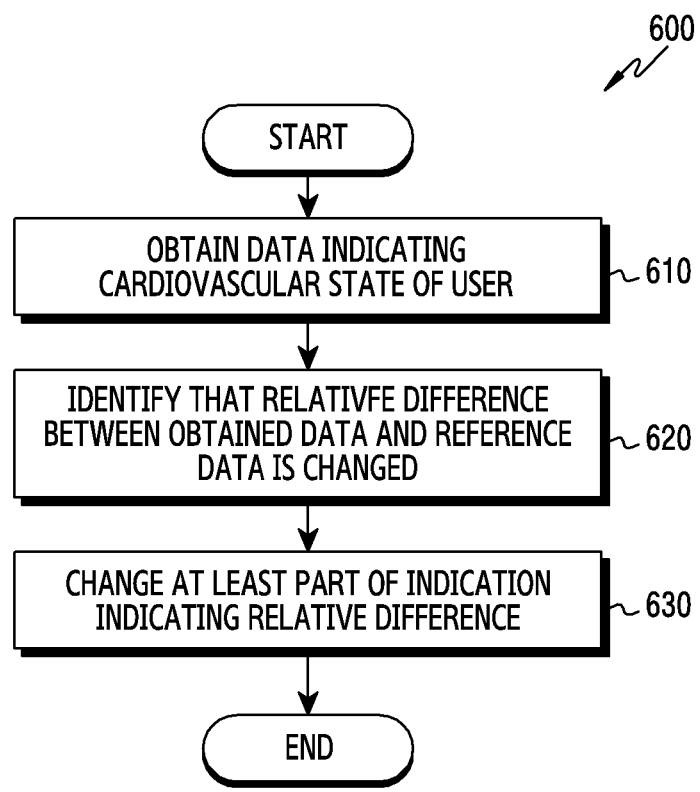
FIG. 6 illustrates another example of an operation of an electronic device according to various embodiments.

FIG. 6 illustrates another example of an operation of an electronic device according to various embodiments. This operation (e.g., operation 600) may be performed by the electronic device 101 shown in FIG. 1, FIG. 2 or FIG. 3, or the processor 120 of the electronic device 101.

Referring to FIG. 6, in operation 610, the processor 120 may obtain data which indicates a cardiovascular state of a user related with the electronic device 101. In various embodiments, the processor 120 may obtain the data indicating the cardiovascular state of the user by using the at least one biometric sensor 210.

In operation 620, the processor 120 may identify that a relative difference between the obtained data and the reference data is changed. In various embodiments, on the basis of obtaining the data which indicates the cardiovascular state of the user, the processor 120 may compare the obtained data and another data which indicates a user's cardiovascular state having been obtained previously (or lastly) by using the at least one biometric sensor 210. On the basis of the comparison result of the obtained data and the another data, the processor 120 may identify that the relative difference between the obtained data and the reference data is changed. In various embodiments, on the basis of the obtaining of the data, the processor 120 may obtain data which indicates the relative difference between the obtained data and the reference data. The processor 120 may compare data which indicates another relative difference between another data (i.e., data which indicates a user's cardiovascular state having been obtained previously) and the reference data, and the data which indicates the relative difference. On the basis of the comparison result, the processor 120 may identify that the relative difference between the obtained data and the reference data is changed.

In operation 630, on the basis of the identification, the processor 120 may change at least part of an indication which indicates the relative difference displayed using the display 160. For example, referring to FIG. 4C, the processor 120 may change the orientation of the indicator 461-3 included in the indication 461 which indicates the relative difference, and display the indication 461 including the indicator 461-3 having the changed orientation. In various embodiments, by changing only partial data related with the indicator 461-3 (or the indicator 466-3) among frame data for displaying the user interface 460, and updating only the changed partial data to an internal memory (e.g., a graphic random access memory (GRAM)) within a display driving circuit (not shown in FIG. 2), the processor 120 may display the indication 461 (or the indication 466) including the indicator 461-3 (or the indicator 466-3) having the changed orientation. For another example, referring to FIG. 4D, the processor 120 may change a location of the indicator 476-3 included in the indication 476 which indicates the relative difference, and display the indication 476 including the indicator 476-3 disposed in the changed location. In various embodiments, by changing only partial data related with the indicator 476-3 among frame data for displaying the user interface 475, and updating only the changed partial data to the internal memory (e.g., the graphic random access memory (GRAM)) within the display driving circuit (not shown in FIG. 2), the processor 120 may display the indication 475 including the indicator 476-3 having the changed location.

Figure 7A:
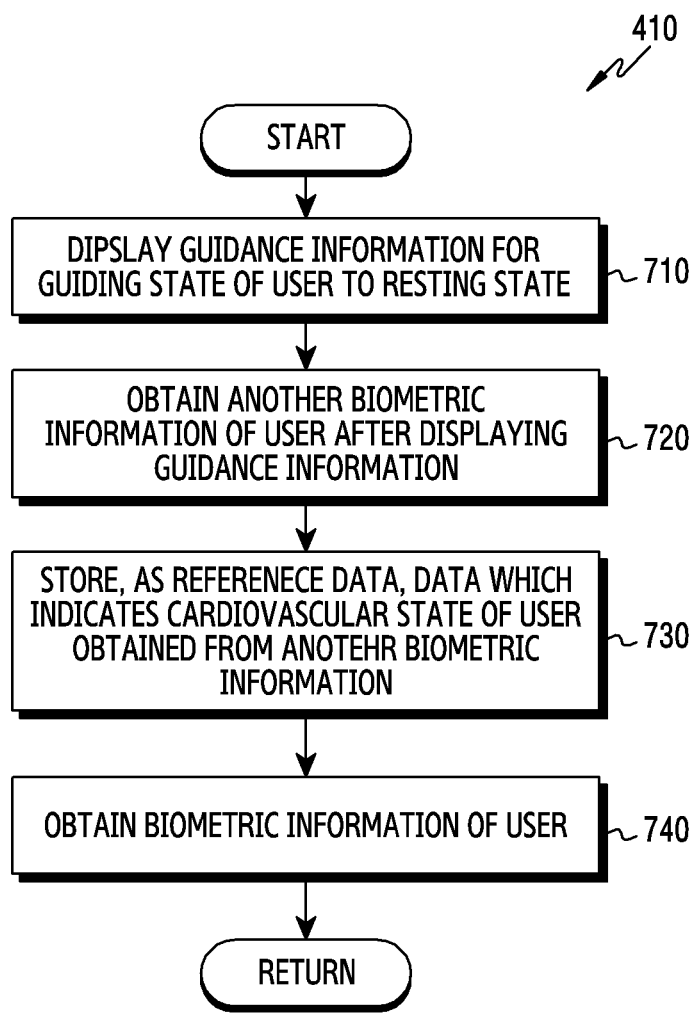
FIG. 7A illustrates an example of an operation of an electronic device obtaining biometric information of a user according to various embodiments.

FIG. 7A illustrates an example of an operation of an electronic device obtaining biometric information of a user according to various embodiments. This operation may be performed by the electronic device 101 shown in FIG. 1, FIG. 2 or FIG. 3, or the processor 120 of the electronic device 101.

Figure 7B:
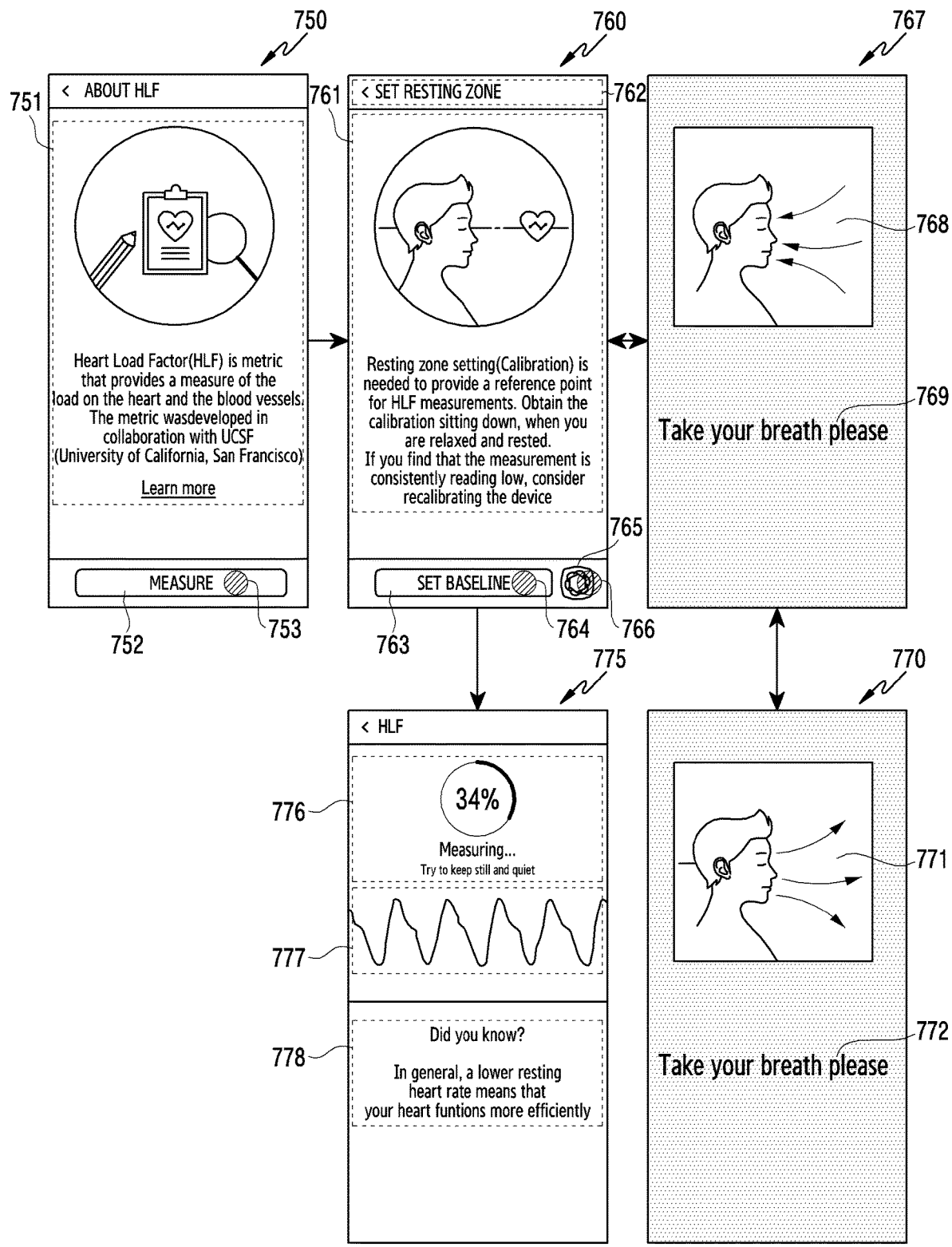
FIG. 7B illustrates another example of a user interface displayed in an electronic device according to various embodiments.

FIG. 7B illustrates another example of a user interface displayed in an electronic device according to various embodiments.

Operation 710 to operation 740 of FIG. 7A may be related with operation 410 of FIG. 4A.

Referring to FIG. 7A, in operation 710, the processor 120 may display guidance information (e.g., breathing guidance information) for guiding a state of a user related with the electronic device 101 to a resting state. In various embodiments, to obtain the reference data, the processor 120 may display the guidance information for guiding the state of the user related with the electronic device 101 to the resting state. For example, referring to FIG. 7B, the processor 120 may display a user interface 750 of an application for presenting a health care service. The user interface 750 may include information 751 for guiding what a heart load factor (HLF) is. In various embodiments, the user interface 750 may further include an object 752 for converting into the user interface 760 for obtaining the reference data. In various embodiments, in response to obtaining of an input 753 for the object 752, the processor 120 may display the user interface 760 converted from the user interface 750. In various embodiments, the user interface 760 may indicate that it is required to obtain the reference data (e.g., set a resting zone), and include information 761 for guiding a posture of the user required for obtaining the reference data. In various embodiments, the user interface 760 may further include information 762 (e.g., SET RESTING ZONE) for making the user recognize that it is the step of obtaining the reference data. In various embodiments, the user interface 760 may further include an icon 763 for initiating the obtaining of the reference data. In various embodiments, the icon 763 may be used to convert the user interface 760 into a user interface 775. For example, in response to obtaining of an input 764 for the object 763, the processor 120 may display the user interface 775 converted from the user interface 760. In various embodiments, the user interface 760 may further include an icon 765 for guiding the user to enter the resting state. In various embodiments, the icon 765 may be used to convert the user interface 760 into a user interface 767. For example, in response to obtaining of an input 766 for the object 765, the processor 120 may display the user interface 767 converted from the user interface 760. In various embodiments, the user interface 767 may include an image 768 for guiding the inspiration of the user and a text 769 for guiding the inspiration of the user. In various embodiments, after displaying the user interface 767 during a specified time, the processor 120 may display a user interface 770 for guiding the expiration of the user. In various embodiments, the user interface 770 may include an image 771 for guiding the expiration of the user and a text 772 for guiding the expiration of the user. In various embodiments, after displaying the user interface 770 during a specified time, the processor 120 may again display the user interface 767 for guiding the inspiration of the user. In various embodiments, by repeatedly alternately displaying the user interface 767 and the user interface 770, the processor 120 may display the guidance information.

In operation 720, after displaying the guidance information, the processor 120 may obtain another biometric information of the user. In various embodiments, the another biometric information may mean biometric information of the user who is in the resting state. In various embodiments, while obtaining the another biometric information, the processor 120 may display, through the display 160, information which indicates a state of obtaining of the another biometric information. For example, referring to FIG. 7B, the processor 120 may display the user interface 775 by the information which indicates the state of obtaining of the another biometric information. In various embodiments, the processor 120 may display a progress bar 776 for indicating a degree of obtaining of the another biometric information, a wave form 777 identified from the another biometric information which is being obtained, and the user interface 775 including health information 778 related with a cardiovascular state.

In operation 730, the processor 120 may store, as the reference data, data which indicates a cardiovascular state of the user obtained from the another biometric information.

In operation 740, after storing the reference data, the processor 120 may obtain biometric information of the user by using at least one biometric sensor 210, in order to obtain the first data.

FIG. 7A illustrates an example of obtaining the another biometric information after displaying the guidance information, but this is for description convenience. In various embodiments, it should be noted that the processor 120 may obtain the another biometric information without the operation of displaying the guidance information.

As described above, the processor 120 of the electronic device 101 of various embodiments may obtain the reference data by using at least one biometric sensor 210. To obtain the biometric information of the user of the resting state, the processor 120 of the electronic device 101 may present the guidance information.

Figure 8:
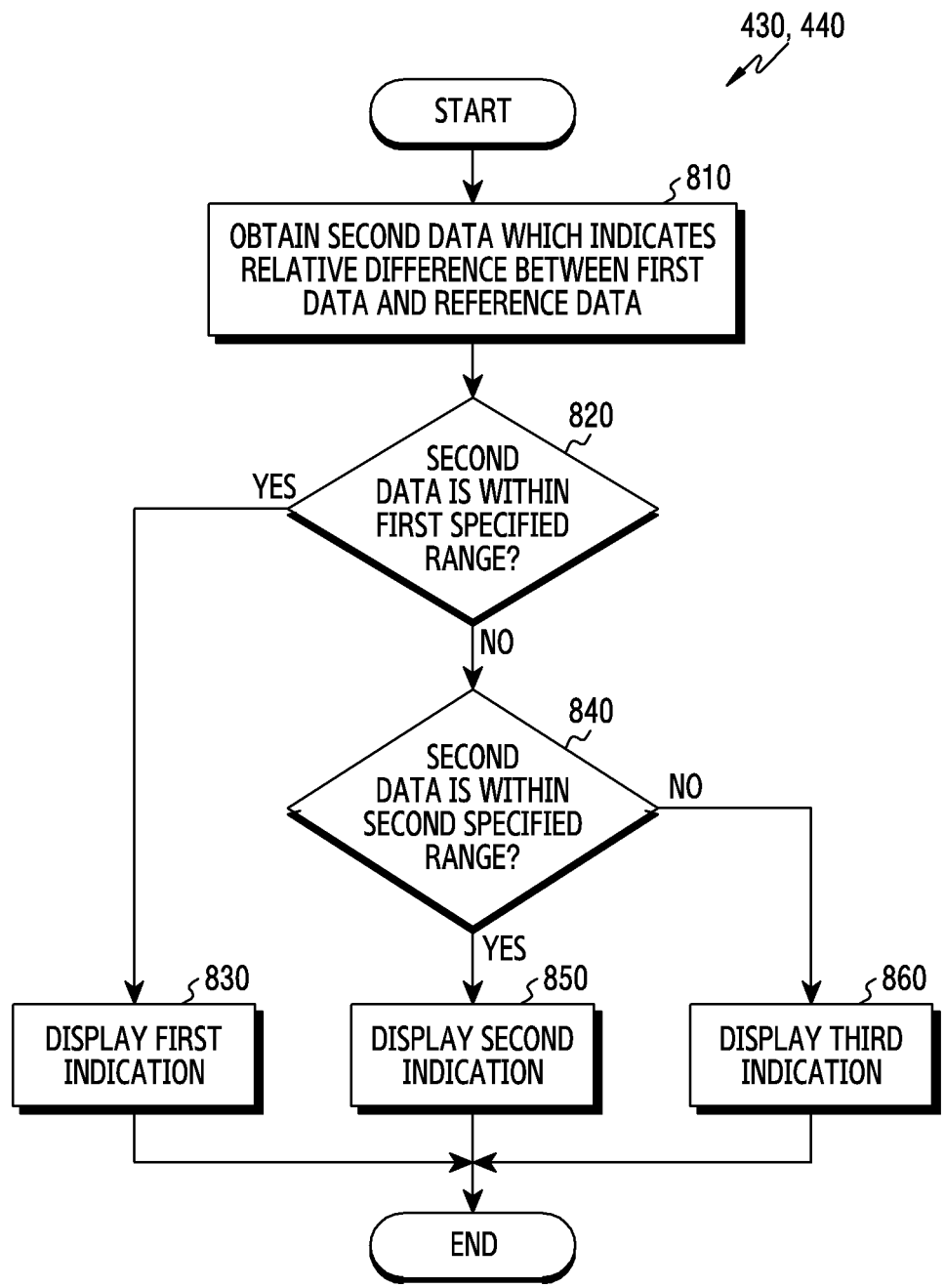
FIG. 8 illustrates an example of an operation of an electronic device obtaining second data and displaying an indication related with the second data according to various embodiments.

FIG. 8 illustrates an example of an operation of an electronic device obtaining second data and displaying an indication related with the second data according to various embodiments. This operation may be performed by the electronic device 101 shown in FIG. 1, FIG. 2 or FIG. 3, or the processor 120 of the electronic device 101.

Operation 810 to operation 860 of FIG. 8 may be related with operation 430 and operation 440 of FIG. 4A.

Referring to FIG. 8, in operation 810, the processor 120 may obtain second data which indicates a relative difference between first data and reference data. In various embodiments, each of the first data, the reference data, and the second data may correspond to each of the first data, the reference data, and the second data described through FIG. 2. In various embodiments, operation 810 may correspond to operation 430 of FIG. 4A.

In operation 820, the processor 120 may identify whether the second data is within a first specified range. In various embodiments, the first specified range may be configured to identify whether a cardiovascular state of the user is a normal state. In various embodiments, the first specified range may be identified on the basis at least of a bodily characteristic of the user or the reference data. In various embodiments, the first specified range may be configured through an input of the user as well. In response to the second data being within the first specified range, the processor 120 may perform operation 830. Unlike this, in response to the second data being outside of the first specified range, the processor 120 may perform operation 840.

In operation 830, the processor 120 may display a first indication through the display 160 on the basis of identifying that the second data is within the first specified range. The first indication may indicate a health status of the user, and may indicate that the cardiovascular state of the user is within a normal range.

In operation 840, the processor 120 may identify whether the second data is within a second specified range, on the basis of identifying that the second data is outside of the first specified range. The second specified range may be configured to identify whether the cardiovascular state of the user is a state belonging to a high-risk group or is a state belonging to a low-risk group. In various embodiments, the second specified range may be configured to identify whether the cardiovascular state of the user is a state belonging to a risk group or is a better state. In various embodiments, the second specified range may be identified on the basis of a bodily characteristic of the user or the reference data. In various embodiments, the second specified range may be configured through an input of the user as well. In response to the second data being within the second specified range, the processor 120 may perform operation 850. Unlike this, in response to the second data being outside of the second specified range, the processor 120 may perform operation 860.

In operation 850, the processor 120 may display a second indication distinct from the first indication through the display 160, on the basis of identifying that the second data is within the second specified range. In various embodiments, in response to the second specified range being configured to identify whether the cardiovascular state of the user is a state belonging to a high-risk group or is a state belonging to a low-risk group, the second indication may indicate the health status of the user, and indicate that the cardiovascular state of the user is the state belonging to the low-risk group. In various embodiments, in response to the second specified range being configured to identify whether the cardiovascular state of the user is a state belonging to a risk group or is a better state, the second indication may indicate the health status of the user, and indicate that the cardiovascular state of the user is a state better than before.

In operation 860, the processor 120 may display, through the display 160, a third indication distinct from the first indication and the second indication, on the basis of identifying that the second data is outside of the second specified range. In various embodiments, in response to the second specified range being configured to identify whether the cardiovascular state of the user is a state belonging to a high-risk group or is a state belonging to a low-risk group, the second indication may indicate the health status of the user, and indicate that the cardiovascular state of the user is the state belonging to the high-risk group. In various embodiments, in response to the second specified range being configured to identify whether the cardiovascular state of the user is a state belonging to a risk group or is a better state, the second indication may indicate the health status of the user, and indicate that the cardiovascular state of the user is the state belonging to the risk group.

As described above, the processor 120 of the electronic device 101 of various embodiments may present a mutually different indication according to a range which the second data belongs to. The electronic device 101 of various embodiments may present a mutually different indication on the basis of the second data, wherein a user may intuitively recognize the cardiovascular state of the user.

Figure 9:
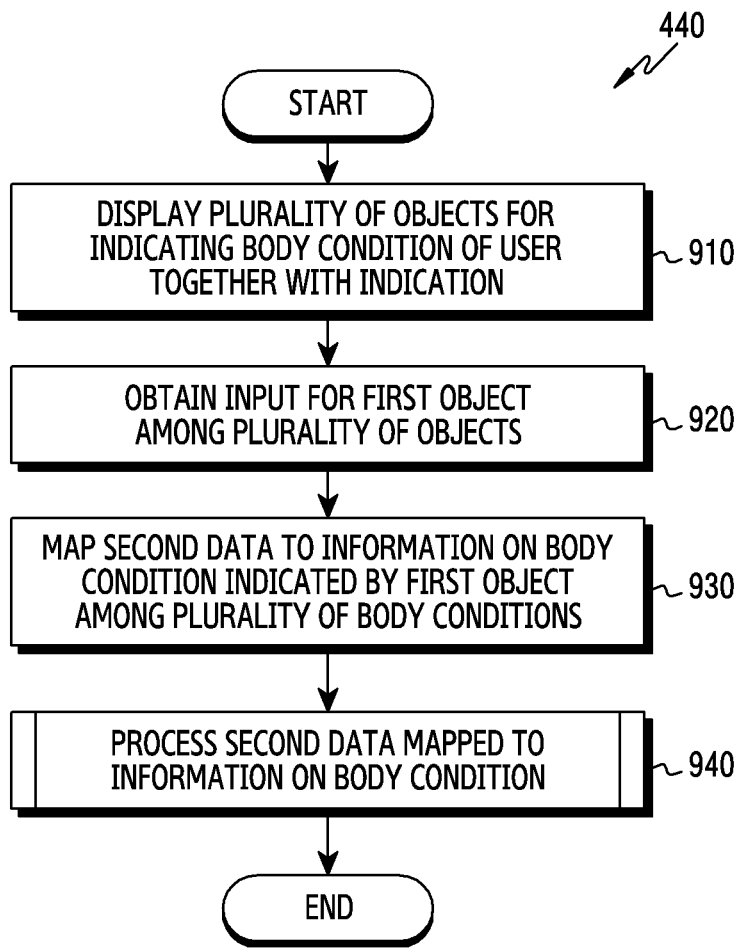
FIG. 9 illustrates an example of an operation of an electronic device processing second data according to various embodiments.

FIG. 9 illustrates an example of an operation of an electronic device processing second data according to various embodiments. This operation may be performed by the electronic device 101 shown in FIG. 1, FIG. 2 or FIG. 3, or the processor 120 of the electronic device 101.

Operation 910 to operation 940 of FIG. 9 may be related with operation 440 of FIG. 4A.

Referring to FIG. 9, in operation 910, the processor 120 may display a plurality of objects for indicating the body condition of the user during the course of obtaining the biometrical information, together with the indication. For example, referring to FIG. 4C, the processor 120 may display the plurality of objects 462, together with the indication 461, within the user interface 460. Each of the plurality of objects 462 may indicate each of the plurality of body conditions defined in the electronic device 101.

In operation 920, the processor 120 may obtain an input for a first object among the plurality of objects. For example, the processor 120 may obtain a touch input for the first object received through the display 160.

In operation 930, the processor 120 may map the second data to information on a body condition indicated by the first object among the plurality of objects. For example, in response to the first object indicating being tired, the processor 120 may map the second data to information which indicates being tired. In various embodiments, the processor 120 may classify the second data by body condition.

In operation 940, the processor 120 may process the second data mapped to the information on the body condition. In various embodiments, by storing the second data mapped to the information on the body condition, the processor 120 may process the second data. In various embodiments, by transmitting the second data mapped to the information on the body condition to an external electronic device, the processor 120 may process the second data. However, an embodiment is not limited to this.

As described above, the processor 120 of the electronic device 101 of various embodiments may classify the second data on the basis of the body condition of the user during the course of obtaining the biometric information. The processor 120 of the electronic device 101 of various embodiments may classify the second data on the basis of the body condition of the user, because the cardiovascular state may be varied according to the body condition of the user.

Figure 10:
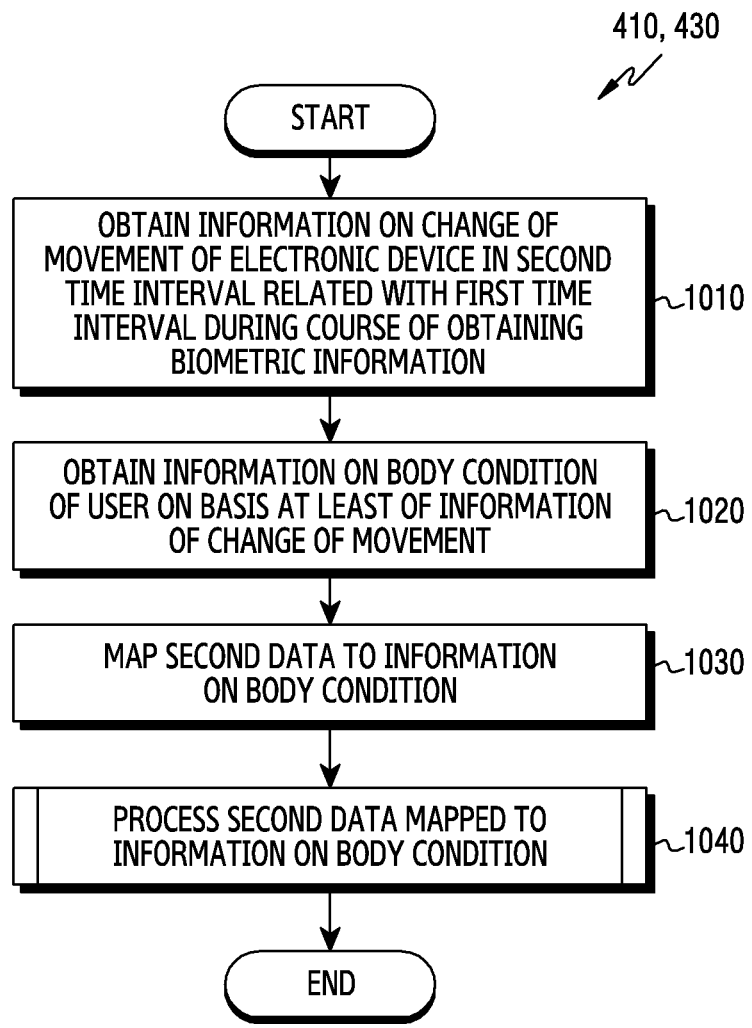
FIG. 10 illustrates another example of an operation of an electronic device processing second data according to various embodiments.

FIG. 10 illustrates another example of an operation of an electronic device processing second data according to various embodiments. This operation may be performed by the electronic device 101 shown in FIG. 1, FIG. 2 or FIG. 3, or the processor 120 of the electronic device 101.

Operation 1010 to operation 1040 of FIG. 10 may be related with operation 410 and operation 430 of FIG. 4A.

Referring to FIG. 10, in operation 1010, by using the motion sensor 220, the processor 120 may obtain information on a change of movement of the electronic device 101 in a second time interval related with a first time interval during which the biometric information is obtained. In various embodiments, the processor 120 may activate the motion sensor 220 on the basis of identifying that an application presenting a service related with health is executed, and obtain the information on the change of the movement of the electronic device 101 in the second time interval by using the activated motion sensor 220. In various embodiments, the processor 120 may activate the motion sensor 220 on the basis of identifying that a cardiovascular related function of the application is executed, and obtain the information on the change of the movement of the electronic device 101 in the second time interval by using the activated motion sensor 220. In various embodiments, the second time interval may correspond to the first time interval as well, and may be included in the first time interval as well, and may include the first time interval as well. In various embodiments, the second time interval may be at least partially overlapped with the first time interval as well.

In operation 1020, the processor 120 may obtain information on a body condition of the user in the first time interval, on the basis at least of the information on the change of the movement. For example, the processor 120 may identify that the body condition of the user is after exercise on the basis of the information on the change of the movement, and obtain the information which indicates that the body condition of the user in the first time interval is after exercise. For another example, by identifying that the first data is outside of a reference range, the processor 120 may identify that the body condition of the user is during exercise and, on the basis of the identification, obtain the information which indicates that the body condition of the user in the first time interval is during exercise. For further example, the processor 120 measure a degree of stress of a user, and identify that the body condition of the user is a tired state (or a wearied state, a rigid state, a tension state, etc.) on the basis of the measured degree, and obtain the information which indicates that the body condition of the user in the first time interval is the tired state.

In operation 1030, the processor 120 may map the second data to the information on the body condition.

In operation 1040, the processor 120 may process the second data mapped to the information on the body condition. Operation 1040 may correspond to operation 940 of FIG. 9.

In aspect of not requiring a user input, operation 1010 to operation 1040 may be distinct from operation 910 to operation 940 of FIG. 9.

Figure 11:
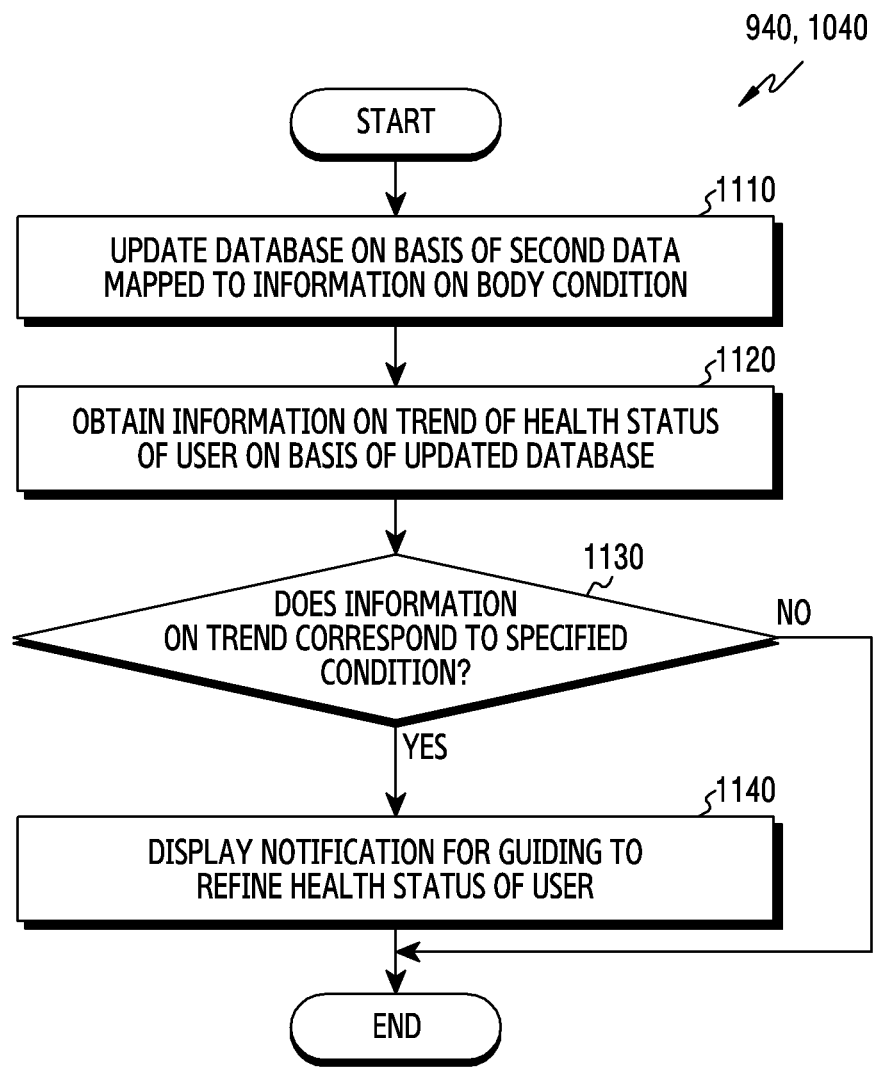
FIG. 11 illustrates an example of an operation of an electronic device displaying a notification by processing second data mapped to a body condition of a user according to various embodiments.

FIG. 11 illustrates an example of an operation of an electronic device displaying a notification by processing second data mapped to a body condition of a user according to various embodiments. This operation may be performed by the electronic device 101 shown in FIG. 1, FIG. 2 or FIG. 3, or the processor 120 of the electronic device 101.

Operation 1110 to operation 1140 of FIG. 11 may be related with each of operation 940 of FIG. 9 and operation 1040 of FIG. 10.

Referring to FIG. 11, in operation 1110, the processor 120 may update a database for recording a health status of the user, on the basis of the second data mapped to the information on the body condition. In various embodiments, the database may be stored in the memory 130. In various embodiments, the database may be stored in an external electronic device (e.g., a server) related with the electronic device 101. In this case, the processor 120 may transmit the second data mapped to the information on the body condition, to the external electronic device, and the external electronic device may update a database on the basis of the second data mapped to the information on the body condition.

In operation 1120, the processor 120 may obtain information on a trend of the health status of the user, on the basis of the updated database. For example, the processor 120 may obtain the information on the trend of the health status of the user represented like the another indication 468 or the detailed information 469 shown in FIG. 4D, on the basis of the updated database. In various embodiments, in response to the database being stored in the external electronic device, the information on the trend may be obtained from the external electronic device. In various embodiments, in response to the database being stored in the external electronic device, the information on the trend may be obtained within the external electronic device by the external electronic device as well.

In operation 1130, the processor 120 may identify whether the information on the trend corresponds to a specified condition. To identify whether a trend of a cardiovascular state of the user is a normal state, the specified condition may be configured in the electronic device 101. For example, the processor 120 may identify whether the second data is in a continuously increased state (or decreased state) on the basis of the information on the trend, and identify that the trend of the cardiovascular state of the user is not the normal state on the basis of identifying that the second data is in the continuously increased state (or decreased state). In various embodiments, in response to the database being stored in the external electronic device, and the information on the trend being obtained within the external electronic device, operation 1130 may be performed by the external electronic device as well.

In response to identifying that the information on the trend corresponds to the specified condition, the processor 120 may perform operation 1140.

In operation 1140, the processor 120 may display a notification for guiding to refine the health status of the user, on the basis of identifying that the information on the trend corresponds to the specified condition. In various embodiments, in response to the database being stored in the external electronic device, and the information on the trend being obtained within the external electronic device, and the external electronic device identifying that the information on the trend corresponds to the specified condition, the external electronic device may transmit a message which indicates that the information on the trend corresponds to the specified condition, to the electronic device 101, or transmit a message for displaying the notification in the electronic device 101, to the electronic device 101. The processor 120 may display the notification, on the basis of the message received from the external electronic device.

As described above, to present information of the health status of the user, the electronic device 101 of various embodiments may monitor a trend of the health status related with a cardiovascular state of the user, and present a notification according to the monitoring result.

Figure 12:
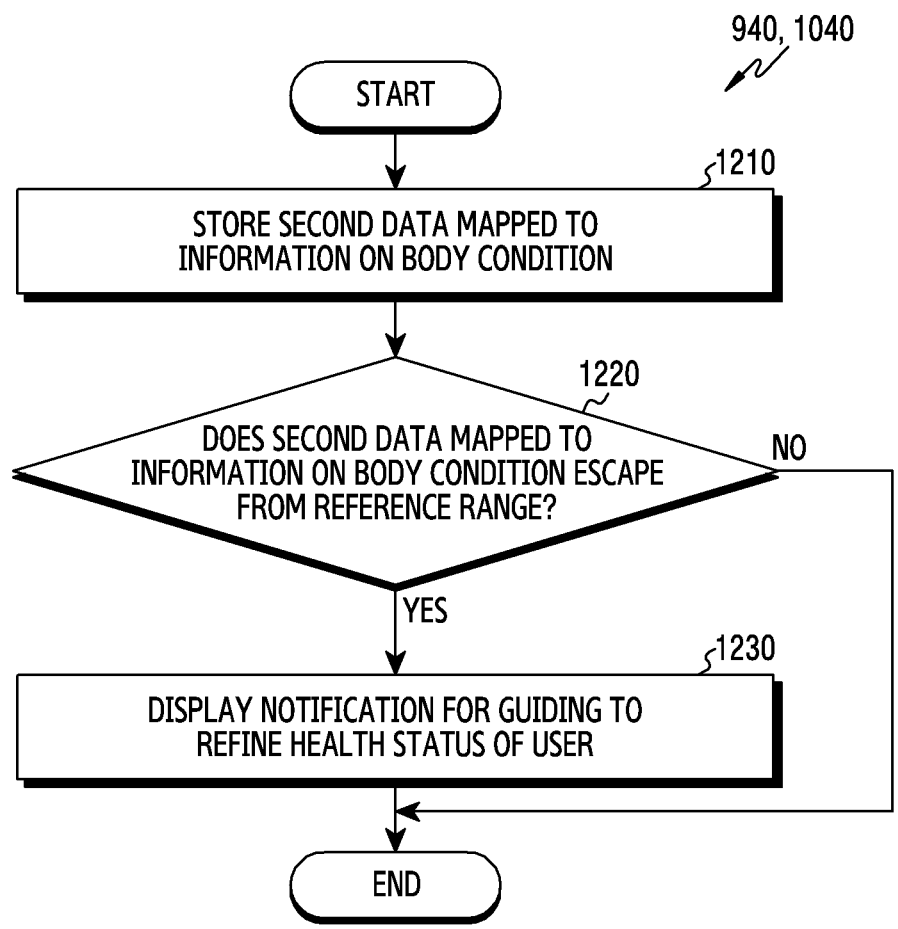
FIG. 12 illustrates another example of an operation of an electronic device displaying a notification by processing second data mapped to a body condition of a user according to various embodiments.

FIG. 12 illustrates another example of an operation of an electronic device displaying a notification by processing second data mapped to a body condition of a user according to various embodiments. This operation may be performed by the electronic device 101 shown in FIG. 1, FIG. 2 or FIG. 3, or the processor 120 of the electronic device 101.

Operation 1210 to operation 1230 of FIG. 12 may be related with each of operation 940 of FIG. 9 and operation 1040 of FIG. 10.

Referring to FIG. 12, in operation 1210, the processor 120 may store, in the memory 130, the second data mapped to the information on the body condition. In various embodiments, to process the second data mapped to the information on the body condition, the processor 120 may store or temporally store the second data mapped to the information on the body condition, in the memory 130.

In operation 1220, the processor 120 may identify whether the second data mapped to the information on the body condition escapes from a reference range. In various embodiments, the reference range may be configured in the electronic device 101 in order to identify whether the cardiovascular state of the user at a time point of obtaining the biometric information, a time point of obtaining the first data, or a time point of obtaining the second data is a risk state. For example, in response to it being judged that a user of a high blood pressure is doing excessive exercise, the reference range may be configured in the electronic device 101 in order to restrict the exercise of the user. In response to the second data mapped to the information on the body condition escaping from the reference range, the processor 120 may perform operation 1230.

In operation 1230, the processor 120 may display a notification for guiding to refine a health status of the user, on the basis of identifying that the second data mapped to the information on the body condition escapes from the reference range. For example, to guide to refine the health status of the user, the processor 120 may display the notification which indicates to stop the exercise of the user, through the display 160.

In comparison with the operations exemplified through FIG. 11, operations exemplified through FIG. 12 may be performed to monitor the health status of the user at a time point of obtaining of the biometric information. By not only presenting the notification on the basis of the trend of the cardiovascular state of the user as in FIG. 11 but also presenting the notification on the basis of the cardiovascular state of the user of a time point of obtaining information through the at least one biometric sensor 210 as in FIG. 12, the electronic device 101 of various embodiments may present a better health service.

Figure 13:
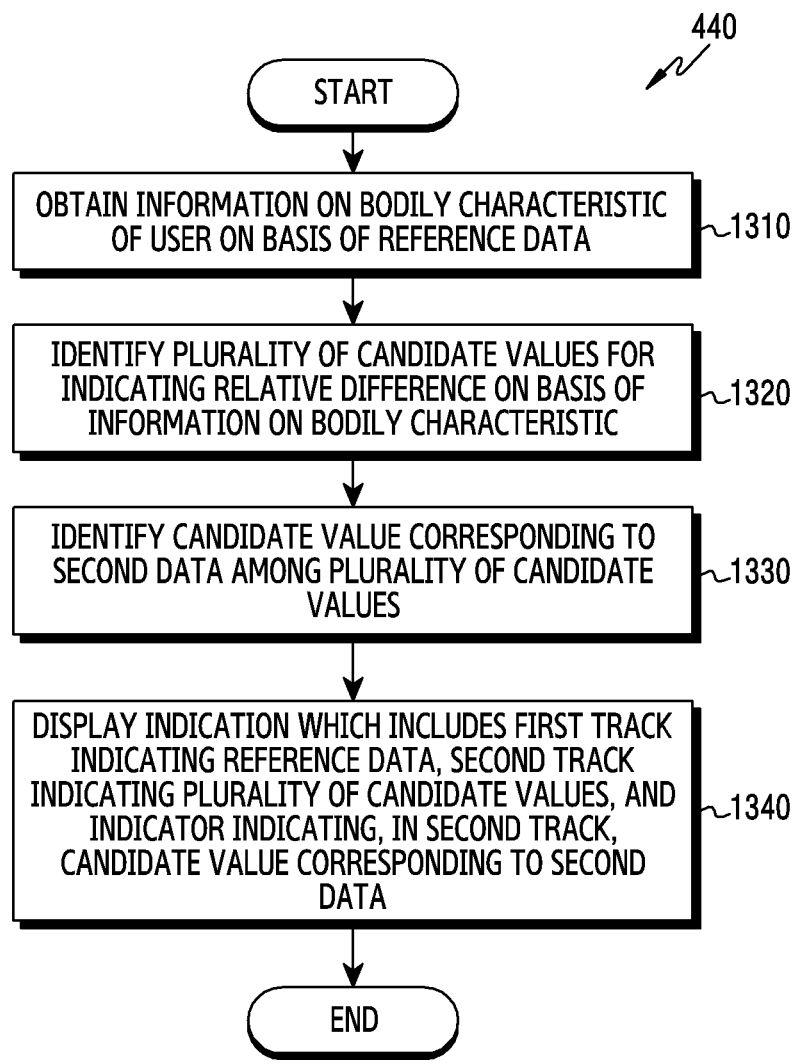
FIG. 13 illustrates an example of an operation of an electronic device configuring a plurality of candidate values related with an indication according to various embodiments.

FIG. 13 illustrates an example of an operation of an electronic device configuring a plurality of candidate values related with an indication according to various embodiments. This operation may be performed by the electronic device 101 shown in FIG. 1, FIG. 2 or FIG. 3, or the processor 120 of the electronic device 101.

Operation 1310 to operation 1340 of FIG. 13 may be related with operation 440 of FIG. 4A.

Referring to FIG. 13, in operation 1310, the processor 120 may obtain information on a bodily characteristic of the user on the basis of the reference data. For example, the processor 120 may obtain the information on the bodily characteristic of the user, by identifying that the user has a high blood pressure from the reference data. For another example, the processor 120 may obtain the information on the bodily characteristic of the user, by identifying that the user has a normal blood pressure from the reference data.

In operation 1320, the processor 120 may identify a plurality of candidate values for indicating the relative difference, on the basis of the information on the bodily characteristic. In various embodiments, the plurality of candidate values may be used for displaying of the second track. The processor 120 may differently configure a range of the plurality of candidate values according to the bodily characteristic of the user, or differently configure sections between the plurality of candidate values. For example, in response to the bodily characteristic of the user being identified as the normal blood pressure, the processor 120 may configure the range of the plurality of candidate values as 1.0 to 2.0 in the second track. In response to the bodily characteristic of the user being identified as the high blood pressure, the processor 120 may configure the range of the plurality of candidate values as 1.0 to 1.5 in the second track. For another example, in response to the bodily characteristic of the user being identified as the normal blood pressure, the processor 120 may configure sections between the plurality of candidate values as a first section having a range of 1.0 to 1.5 and a second section having a range of 1.5 to 2.0 in the second track. In response to the bodily characteristic of the user being identified as the high blood pressure, the processor 120 may configure the sections between the plurality of candidate values as a first section having a range of 1.0 to 1.2 and a second section having a range of 1.2 to 2.0 in the second track. However, an embodiment is not limited to this.

In operation 1330, the processor 120 may identify a candidate value corresponding to the second data among the plurality of candidate values. To indicate the second data through the indication, the processor 120 may identify the candidate value corresponding to the second data among the plurality of candidate values.

In operation 1340, the processor 120 may display the indication which includes a first track which indicates the reference data, a second track which indicates the plurality of candidate values, and an indicator which indicates the candidate value corresponding to the second data in the second track. For example, referring to FIG. 4C, the processor 120 may display the indication 461 which includes the first track 461-1 and second track 461-2 configured with at least either part of a ring or a curve, and the indicator 461-3 indicating a candidate value corresponding to the second data in the second track 461-2. For another example, referring to FIG. 4D, the processor 120 may display the indication 466 which includes the first track 466-1 and second track 466-2 configured with a bar, and the indicator 466-3 indicating the candidate value corresponding to the second data in the second track 466-2.

As described above, the electronic device 101 of various embodiments may present a refined visibility to the user, by changing the displaying of the indication on the basis of the bodily characteristic of the user. The electronic device 101 of various embodiments may present a better user experience (UX) through the adjustment of the displaying of the indication.

A method of an electronic device of various embodiments described above may include a first operation of receiving first data by using the PPG sensor and determining a plurality of reference ranges of a blood pressure on the basis at least in part of the first data, and storing the plurality of reference ranges, and a second operation of, after the first operation, receiving second data by using the PPG sensor, and selecting one reference range among the plurality of reference ranges on the basis at least in part of the second data, and presenting at least one of a graphical user interface (GUI), a text, or a numerical value in order to indicate the selected reference range among the plurality of reference ranges on the display.

In various embodiments, determining the plurality of reference ranges may include determining the plurality of ranges on the basis at least of pulse wave analysis (PWA) for the first data. In various embodiments, determining the plurality of reference ranges may include using at least one of a systolic blood pressure (SBP) value, a diastolic blood pressure (DBP) value, a mean arterial pressure (MAP) value, a cardiac output (CO) value, a total peripheral resistance (TPR), or a resting heart rate (RHR) within the PWA.

In various embodiments, the first operation may include presenting a user guide on the display before receiving the first data.

A method of an electronic device of various embodiments described above may include obtaining biometric information of a user related with the electronic device by using the at least one biometric sensor of the electronic device, obtaining first data indicating a cardiovascular state of the user from the biometric information, obtaining second data indicating a relative difference between the first data and reference data indicating a cardiovascular state in a resting state of the user, and displaying, by using the display, an indication for indicating a health status of the user, on the basis at least of the second data.

In various embodiments, the method may further include displaying guidance information for guiding a state of the user to the resting state by using the display, and after displaying the guidance information, obtaining another biometric information of the user by using the at least one biometric sensor, and storing, as the reference data, data indicating a cardiovascular state of the user obtained from the another biometric information.

In various embodiments, the method may further include receiving the reference data from an external electronic device by using a communication module of the electronic device.

In various embodiments, displaying the indication may include displaying the indication which includes a first track indicating the reference data, a second track indicating a plurality of candidate values, and an indicator indicating, in the second track, a candidate value corresponding to the second data among the plurality of candidate values, on the basis at least of the second data. For example, the second track may be displayed next to the first rack, and the indicator may be configured with an arrow indicating the candidate value corresponding to the second data among the plurality of candidate values. For example, the first track and the second track may be configured with at least part of a ring. For another example, the first track and the second track may be configured with a bar.

In various embodiments, displaying the indication may include displaying a plurality of objects for recording, in the electronic device, a body condition of the user during the course of obtaining the biometric information by using the at least one biometric sensor, together with the indication. Each of the plurality of objects may indicate each of a plurality of body conditions defined in the electronic device. In various embodiments, the method may include obtaining an input for a first object among the plurality of objects, and in response to the obtaining, mapping the second data to information on a body condition indicated by the first object among the plurality of body conditions, and storing, in the memory, the second data mapped to the information on the body condition. In various embodiments, the method may further include updating a database for recording a health status of the user, on the basis of the second data mapped to the information on the body condition, obtaining information on a trend of the health status of the user, on the basis of the updated database, and displaying a notification for guiding to refine the health status of the user, on the basis of that the obtained information on the trend corresponds to at least one specified condition.

In various embodiments, the method may include obtaining information on a change of movement of the electronic device, by using at least one sensor of the electronic device, within a second time interval related with a first time interval during which the biometric information is obtained, obtaining information on a body condition of the user in the first time interval, on the basis at least of the information on the change of the movement of the electronic device, mapping the second data to the information on the body condition, and storing, in the memory, the second data mapped to the information on the body condition. In various embodiments, the method may further include updating a database for recording the health status of the user, on the basis of the second data mapped to the information on the body condition, obtaining information on a trend of the health status of the user, on the basis of the updated database, and displaying a notification for guiding to refine the health status of the user, on the basis of that the obtained information on the trend corresponds to at least one specified condition.

In various embodiments, the method may further include identifying that the second data is outside of a specified range, and in response to the identification, displaying a notification for guiding to refine the health status of the user.

A method of an electronic device of various embodiments described above may include receiving first data indicating a cardiovascular state of a user which has been obtained on the basis of biometric information of the user obtained through at least one biometric sensor of another electronic device, from the another electronic device interworking with the electronic device and worn by the user related with the electronic device, obtaining second data indicating a relative difference between the first data and reference data indicating a cardiovascular state in a resting state of the user, obtaining an input for executing an application presenting a service related with a health stored in the electronic device, and displaying, through the display, an indication for indicating the health status of the user, by using the second data, on the basis of the obtaining.

In various embodiments, the at least one biometric sensor of the another electronic device may be exposed through at least part of a housing of the another electronic device, in order to get in contact with at least part of a body of the user.

In various embodiments, the method may include receiving information on a change of movement of the another electronic device obtained through at least one sensor of the another electronic device within a second time interval related with a first time interval during the course of obtaining the biometric information, from the another electronic device, and obtaining information on a body condition of the user within the first time interval, on the basis at least of the information of the change of the movement of the another electronic device, and mapping the second data to information on the body condition, and storing the second data mapped to the information on the body condition in the memory.

In various embodiments, the method may further include receiving information of a body condition of the user during the course of obtaining the biometric information, from the another electronic device, mapping the second data to the information on the body condition, and storing the second data mapped to the information on the body condition in the memory. The information on the body condition may be obtained by the another electronic device, on the basis of the information on a change of movement of the another electronic device which has been obtained through at least one sensor of the another electronic device within a second time interval related with a first time interval during the course of obtaining the biometric information.

In various embodiments, in response to a remaining capacity of a battery of the another electronic device being within a specified range, the biometric information of the user may be transmitted from the another electronic device to the electronic device on the basis of a first communication technique. In response to the remaining capacity of the battery of the another electronic device being outside of the specified range, the biometric information of the user may be transmitted from the another electronic device to the electronic device on the basis of a second communication technique distinct from the first communication technique.

In various embodiments, a user account of the electronic device may correspond to a user account of the another electronic device.

A method of an electronic device of various embodiments described above may include obtaining data indicating a cardiovascular state of a user related with the electronic device by using the at least one biometric sensor of the electronic device, identifying that a relative difference between the data and reference data indicating a cardiovascular state in a resting state of the user is changed, and changing at least part of an indication indicating the relative difference indicated using the display, on the basis of the identification.

Methods of embodiments mentioned in claims of the present disclosure or the specification thereof may be implemented in the form of hardware, software, or a combination of hardware and software.

When implemented in software, a computer readable storage medium storing one or more programs (software modules) may be provided. One or more programs stored on a computer-readable storage medium are configured for execution by one or more processors in an electronic device. One or more programs include instructions that cause an electronic device to execute methods according to embodiments described in the claims or specification of this disclosure.

Such programs (software modules, software) can be stored in non-volatile memory including random access memory and flash memory, read only memory (ROM), electronic erasable programmable read only memory (EEPROM), magnetic disc storage device, compact disc-ROM (CD-ROM), digital versatile discs (DVDs) or other forms of optical storage device and a magnetic cassette. Or, it may be stored in a memory composed of a combination of some or all of them. Also, a plurality of configuration memories may be included.

In addition, the program may be stored in an attachable storage device that can be accessed through a communication network such as the Internet, an Intranet, a local area network (LAN), a wide LAN (WLAN), or a storage area network (SAN), or a combination thereof. Such a storage device can access a device performing an embodiment of the present disclosure through an external port. In addition, a separate storage device on the communication network may access a device performing an embodiment of the present disclosure.

In the specific embodiments of the present disclosure described above, elements included in the disclosure are expressed in singular or plural according to the specific embodiments presented. However, the singular or plural expressions are appropriately selected for the situation presented for convenience of description, and the present disclosure is not limited to the singular or plural components, and even a component expressed in plural may be composed of a singular, or a component represented in singular may be composed of plural.

Meanwhile, in the detailed description of the present disclosure, specific embodiments have been described. However, various modifications are possible without departing from the scope of the present disclosure. Therefore, the scope of the present disclosure should not be limited to the described embodiments, but should be determined not only by the scope of claims to be described later, but also by the scope and equivalents of the claims.

The invention claimed is:

1. An electronic device comprising:
    a memory storing instructions;
    at least one biometric sensor;
    a display; and
    at least one processor, wherein the at least one processor is configured to execute the stored instructions in order to:
    obtain biometric information of a user related with the electronic device by using the at least one biometric sensor;
    obtain first data indicating a cardiovascular state of the user from the biometric information;
    obtain second data indicating a relative difference between the first data and reference data indicating a cardiovascular state in a resting state of the user; and
    display, by using the display, an indication for indicating a health status of the user, based on at least the second data,
    wherein the at least one processor is further configured to:
        identify a bodily characteristic of the user based on at least the reference data,
        determine at least one of a distribution of plurality of candidate values or a range of the plurality of candidate values based on the bodily characteristic, wherein the plurality of candidate values comprise values that are expected to be acquired as the relative difference as the first data is obtained based at least on the bodily characteristic,
        determine at least one object indicating at least one of the distribution of the plurality of candidate values or the range of the plurality of candidate values and included in a second track indicating the plurality of candidate values, and
    wherein the indication comprises a first track indicating the reference data, the second track extending from the first track, and an indicator indicating, on the second track, a value corresponding to the second data among the plurality of candidate values based on obtaining the second data.

2. The electronic device of claim 1, wherein the at least one processor is further configured to execute the stored instructions in order to:
    display guidance information for guiding a state of the user to the resting state, by using the display;

after displaying the guidance information, obtain another biometric information of the user by using the at least one biometric sensor; and store, as the reference data, data indicating a cardiovascular state of the user obtained from the another biometric information.

3. The electronic device of claim 1, wherein the second track is displayed next to the first track.

4. The electronic device of claim 3, wherein the first track and the second track are configured with at least part of a ring.

5. The electronic device of claim 3, wherein the first track and the second track are configured with a bar.

6. The electronic device of claim 1, wherein the at least one processor is configured to execute the stored instructions in order to:

display a plurality of objects for recording, in the electronic device, a body condition of the user while obtaining the biometric information by using the at least one biometric sensor, together with the indication, and wherein each of the plurality of objects indicates each of a plurality of body conditions defined in the electronic device.

7. The electronic device of claim 6, wherein the at least one processor is further configured to execute the stored instructions in order to:

obtain an input for a first object among the plurality of objects;

in response to the obtaining, map the second data to information on a body condition indicated by the first object among the plurality of body conditions; and store, in the memory, the second data mapped to the information on the body condition.

8. The electronic device of claim 7, wherein the at least one processor is further configured to execute the stored instructions in order to:

update a database for recording the health status of the user based on the second data mapped to the information on the body condition;

obtain information on a trend of the health status of the user based on the updated database; and display a notification for guiding to refine the health status of the user based on the the obtained information on the trend corresponding to at least one specified condition.

9. The electronic device of claim 1, further comprising at least one sensor distinct from the at least one biometric sensor, wherein the at least one processor is further configured to execute the stored instructions in order to:

obtain information on a change of movement of the electronic device, by using the at least one sensor, within a second time interval related with a first time interval during which the biometric information is obtained;

obtain information on a body condition of the user in the first time interval based on at least of the information on the change of the movement of the electronic device;

map the second data to the information on the body condition; and store, in the memory, the second data mapped to the information on the body condition.

10. The electronic device of claim 9, wherein the at least one processor is further configured to execute the stored instructions in order to:

update a database for recording the health status of the user based on the second data mapped to the information on the body condition;

obtain information on a trend of the health status of the user based on the updated database; and display a notification for guiding to refine the health status of the user based on the obtained information on the trend corresponding to at least one specified condition.

11. The electronic device of claim 1, wherein the at least one processor is further configured to execute the stored instructions in order to:

identify that the second data is outside of a specified range; and in response to the identification, display a notification for guiding to refine the health status of the user.

12. A method for operating an electronic device, comprising:

obtaining biometric information of a user related with the electronic device by using at least one biometric sensor of the electronic device;

obtaining first data indicating a cardiovascular state of the user from the biometric information;

obtaining second data indicating a relative difference between the first data and reference data indicating a cardiovascular state in a resting state of the user;

identifying a bodily characteristic of the user based on at least the reference data;

determining at least one of a distribution of plurality of candidate values or a range of the plurality of candidate values based on the bodily characteristic, wherein the plurality of candidate values comprise values that are expected to be acquired as the relative difference as the first data is obtained based at least on the bodily characteristic;

determining at least one object indicating at least one of the distribution of the plurality of candidate values or the range of the plurality of candidate values and included in a second track indicating the plurality of candidate values; and displaying, by using the display of the electronic device, an indication for indicating a health status of the user, on the basis at least of the second data, wherein the indication comprises a first track indicating the reference data, the second track extending from the first track, and an indicator indicating, on the second track, a value corresponding to the second data among the plurality of candidate values based on obtaining the second data.

13. The method of claim 12, further comprising:

displaying guidance information for guiding a state of the user to the resting state, by using the display;

after displaying the guidance information, obtaining another biometric information of the user by using the at least one biometric sensor; and storing, as the reference data, data indicating a cardiovascular state of the user obtained from the another biometric information.

14. The method of claim 12, wherein the second track is displayed next to the first track.

15. The method of claim 14, wherein the first track and the second track are configured with at least part of a ring.

16. The method of claim 14, wherein the first track and the second track are configured with a bar.

17. The method of claim 12, further comprising:

displaying a plurality of objects for recording, in the electronic device, a body condition of the user while obtaining the biometric information by using the at least one biometric sensor, together with the indication, and wherein each of the plurality of objects indicates each of a plurality of body conditions defined in the electronic device.

18. The method of claim 17, further comprising:

obtaining an input for a first object among the plurality of objects;

in response to the obtaining, mapping the second data to information on a body condition indicated by the first object among the plurality of body conditions; and storing, in a memory, the second data mapped to the information on the body condition.

\* \* \* \* \*